(12) United States Patent
Rajasekhar

(10) Patent No.: US 10,213,411 B2
(45) Date of Patent: *Feb. 26, 2019

(54) USE OF PRODRUGS OF FUMARATES IN TREATING HEART FAILURE DISEASES

(71) Applicant: Vijaykumar Rajasekhar, Apple Valley, CA (US)

(72) Inventor: Vijaykumar Rajasekhar, Apple Valley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/249,820

(22) Filed: Aug. 29, 2016

(65) Prior Publication Data

US 2017/0056372 A1    Mar. 2, 2017

Related U.S. Application Data

(60) Provisional application No. 62/210,730, filed on Aug. 27, 2015.

(51) Int. Cl.
*A61K 31/4015*    (2006.01)
*A61K 45/06*    (2006.01)

(52) U.S. Cl.
CPC .......... *A61K 31/4015* (2013.01); *A61K 45/06* (2013.01)

(58) Field of Classification Search
CPC ........................... A61K 31/4015; A61K 45/06
See application file for complete search history.

(56) References Cited

U.S. PATENT DOCUMENTS

| | | | |
|---|---|---|---|
| 3,580,918 A | 5/1971 | Bodnarjuk et al. | |
| 4,515,974 A | 5/1985 | Zecher et al. | |
| 4,851,439 A | 7/1989 | Speiser et al. | |
| 5,149,695 A | 9/1992 | Speiser et al. | |
| 5,424,332 A | 6/1995 | Speiser et al. | |
| 5,451,667 A | 9/1995 | Speiser et al. | |
| 5,723,558 A | 3/1998 | Oishi et al. | |
| 6,306,900 B1 | 10/2001 | Haeberlin et al. | |
| 6,355,676 B1 | 3/2002 | Joshi et al. | |
| 6,436,992 B1 | 8/2002 | Joshi et al. | |
| 6,509,376 B1 | 1/2003 | Joshi et al. | |
| 7,612,110 B2 | 11/2009 | Joshi et al. | |
| 7,619,001 B2 | 11/2009 | Joshi et al. | |
| 7,803,840 B2 | 9/2010 | Joshi et al. | |
| 7,915,310 B2 | 3/2011 | Joshi et al. | |
| 8,148,414 B2 | 4/2012 | Gangakhedkar et al. | |
| 8,399,514 B2 | 3/2013 | Lukashev et al. | |
| 8,524,773 B2 | 9/2013 | Joshi et al. | |
| 8,669,281 B1 * | 3/2014 | Zeidan .................. | C07D 207/40 514/425 |
| 2003/0018072 A1 | 1/2003 | Joshi et al. | |
| 2004/0054001 A1 | 3/2004 | Joshi et al. | |
| 2007/0027076 A1 * | 2/2007 | Joshi .................... | A61K 31/231 514/310 |
| 2007/0248662 A1 | 10/2007 | Joshi et al. | |
| 2007/0248663 A1 | 10/2007 | Joshi et al. | |
| 2008/0004344 A1 | 1/2008 | Nilsson et al. | |
| 2008/0227847 A1 | 9/2008 | Nilsson et al. | |
| 2008/0233185 A1 | 9/2008 | Joshi et al. | |
| 2008/0299196 A1 | 12/2008 | Nilsson et al. | |
| 2008/0300217 A1 | 12/2008 | Nilsson | |
| 2009/0082260 A1 | 3/2009 | Lamb et al. | |
| 2009/0181085 A1 | 7/2009 | Joshi et al. | |
| 2009/0182047 A1 | 7/2009 | Joshi et al. | |
| 2009/0304790 A1 | 12/2009 | Nilsson et al. | |
| 2011/0124615 A1 | 5/2011 | Joshi et al. | |
| 2013/0004526 A1 | 1/2013 | Joshi et al. | |
| 2015/0265707 A1 | 9/2015 | Manthati et al. | |

FOREIGN PATENT DOCUMENTS

| | | |
|---|---|---|
| CA | 2248955 A1 | 4/1998 |
| WO | 1998052549 A2 | 11/1998 |
| WO | 2002055066 A1 | 7/2002 |
| WO | 2002055067 A2 | 7/2002 |
| WO | 2005023241 A1 | 3/2005 |
| WO | 2006050730 A1 | 5/2006 |
| WO | 2007042034 A1 | 4/2007 |

OTHER PUBLICATIONS

Kavita Sharma, David A. Kass, Heart Failure With Preserved Ejection Fraction Mechanisms, Clinical Features, and Therapies, Circulation Research, 2014, vol. 115, No. 1, pp. 79-96 (Year: 2014).*

Scott L. Hummel, M.D., M.S and Dalane W. Kitzman, M.D., Update on heart failure with preserved ejection fraction, Curr Cardiovasc Risk Rep. Dec. 2013 ; 7(6): 495-502 (Year: 2013).*

Ashrafian et al. article entitled "Fumarate is Cardioprotective via Activation of the Nrf2 Antioxidant Pathway," Cell Metab. Mar. 7, 2012;15(3):361-71.

Pearl et al. article entitled "Fumarate-Enriched Blood Cardioplegia Results in Complete Functional Recovery of Immature Myocardium," Ann. Thorac. Surg. 1993;57:1636-1641, 1994 by the Society of Thoracic Surgeons.

Tavazzi et al. article entitled "Effect of rosuvastatin in patients with chronic heart failure (the GISSI-HF trial): a randomised, double-blind, placebo-controlled trial;" Lancet. Oct. 4, 2008;372(9645):1231-9.

Mudd, et al. article entitled "Tackling heart failure in the twenty-first century," Nature Publishing Group, 2008;451:919-928.

Paulus et al. article entitled "A Novel Paradigm for Heart Failure With Preserved Ejection Fraction: Comorbidities Drive Myocardial Dysfunction and Remodeling Through Coronary Microvascular Endothelial Inflammation," J Am Coll Cardiol 2013; 62: 263-271.

(Continued)

*Primary Examiner* — Sarah Pihonak
*Assistant Examiner* — Jason Deck
(74) *Attorney, Agent, or Firm* — Aurora Consulting LLC; Ashley Sloat

(57) ABSTRACT

Methods and pharmaceutical compositions comprising one or more prodrugs (e.g., aminoalkyl prodrugs) of monomethyl fumarate (MMF) thereof are provided herein for the treatment of a heart failure disease, including heart failure with preserved ejection fraction. The compounds of the present disclosure are configured to be converted in vivo, upon oral administration, to monomethyl fumarate. Upon conversion, the active moiety (i.e., monomethyl fumarate) of various embodiments is effective in treating subjects suffering from a heart failure disease, including heart failure with preserved ejection fraction.

19 Claims, No Drawings

(56) References Cited

OTHER PUBLICATIONS

Pitt et al. article entitled "Spironolactone for Heart Failure with Preserved Ejection Fraction," N Engl J Med. Apr. 10, 2014;370(15):1383-92.
Redfield et al. article entitled "Effect of Phosphodiesterase-5 Inhibition on Exercise Capacity and Clinical Status in Heart Failure with Preserved Ejection Fraction: A Randomized Clinical Trial," JAMA Mar. 27, 2013;309(12):1268-77.
Zhou et al. article entitled "The Role of Nrf2-Mediated Pathway in Cardiac Remodeling and Heart Failure," Oxid Med Cell Longev. 2014;2014:260429.
Zuo et al. article eneitled "Heart failure with preserved ejection fraction: defining the function of ROS and NO," J Appl Physiol. May 14, 2015:jap.01149.2014.
From et al. articled entitled "Heart Failure with Preserved Ejection Fraction: Pathophysiology and Emerging Therapies," Cardiovasc Ther. Aug 2011;29(4):e6-21.
Tecfidera NDA 204063—FDA Approved Labeling Text dated Mar. 27, 2013, Full Prescribing Information, Reference ID: 3283381.
Wikipedia definition "Heart failure with preserved ejection fraction," printed Oct. 19, 2017 from https://web.archive.org/web/20160120183220/https://en.wikipedia.org/wiki/Heart_failure . . .
Mayo Clinic document entitled "Diseases and Conditions Heart Failure," printed Oct. 19, 2017 from https://web.archive.org/web/20151202102715/http://www.mayclinic.org/diseases-condit . . .
Wisegeek article entitled "What Is Cardiac Insufficiency?" printed Oct. 19, 2017 from https://web.archive.org/web/20150506180705/http://www.wisegeekhealth.com/what-is-c . . .

\* cited by examiner

USE OF PRODRUGS OF FUMARATES IN TREATING HEART FAILURE DISEASES

CROSS-REFERENCE TO RELATED APPLICATIONS

This patent application claims priority to U.S. provisional patent application Ser. No. 62/210,730, filed on Aug. 27, 2015, which is herein incorporated by reference in its entirety,

INCORPORATION BY REFERENCE

All publications and patent applications mentioned in this specification are herein incorporated by reference in their entirety, as if each individual publication or patent application was specifically and individually indicated to be incorporated by reference in its entirety.

TECHNICAL FIELD

This disclosure relates to methods and compositions of treating heart failure diseases, including heart failure with preserved ejection fraction, in a subject in need thereof by administering to the subject a therapeutically effective amount of one or more prodrugs of monomethyl fumarate (MMF) alone or in combination with one or more second agents useful for treating heart failure.

BACKGROUND

Heart failure (HF) is major health problem in the United States (U.S.) and elsewhere. In the U.S., HF affects over 5 million people with approximately half a million new cases occurring each year. HF is the leading cause of hospitalizations in people over 65 years in age. HF has many potential causes and diverse clinical features. Symptoms of heart failure can include dyspnea during activity or at rest, cough with white sputum, rapid weight gain, swelling in ankles, legs and abdomen, dizziness, fatigue and weakness, rapid or irregular heartbeats, nausea, palpitations, and chest pains.

About half of heart failure patients have heart failure with preserved ejection fraction (HFPEF). Distinct from traditional HF, i.e., heart failure with reduced ejection fraction (HFREF) in which the ventricle cannot properly contract, patients with HFPEF show declined performance of a heart ventricle, not at the time of contraction (systole), but during the phase of filling (diastole). HFPEF patients show normal ejection fraction of blood pumped out of the ventricle, but the heart muscle does not quickly relax to allow efficient filling of blood returning from the body. Morbidity and mortality of HFPEF are similar to HFREF; however, therapies that benefit HFREF are not effective in treating or preventing HFPEF. Patients with HFPEF have an ejection fraction of $\geq 40\%$, $\geq 45\%$, or $\geq 50\%$ depending on which definition is chosen from the literature. On the other hand, patients with HFREF have an ejection fraction of either $\leq 35\%$ or $\leq 40\%$ depending on which definition and guidelines are used. For ease of simplicity, and not to be limiting in any way, HFPEF can be considered as having an ejection fraction $\geq 40\%$ and HFREF can be considered as having an ejection fraction $< 40\%$.

Other names for the two primary clinical subsets of HF are diastolic heart. failure (DHF) and systolic heart failure (SHF). SHF, which is also known as heart failure with reduced ejection fraction (HFREF), involves an abnormality of the heart resulting in failure of the heart to pump blood at a rate needed for metabolizing tissues at rest and/or during exertion. DHF, which is also known as heart failure with preserved ejection fraction. (HFPEF), is a clinical syndrome with symptoms and signs of HF, a preserved ejection fraction, and abnormal diastolic function. The clinical manifestations of HFREF and HFPEF have distinct differences in risk factors, patient characteristics, and pathophysiology. Moreover, medications proven effective in HFREF have not been found to be effective in HFPEF. At present there are no approved treatments to reduce mortality in HFPEF.

In HFREF, medications such as beta-blockers, ace-inhibitors, angiotensin receptor blockers, isosorbide dinitrate, hydralazine, aldosterone inhibitors, and angiotensin receptor neprilysin inhibitors have been shown to provide benefit. However, these medications have not shown to be beneficial in patients with HFPEF, and are not approved therapies for HFPEF.

Given that there are currently no approved treatments to improve survival in HFPEF, there remains, therefore, an urgent need in the treatment of HFPEF for a product that can improve morbidity and mortality of patients with HFPEF.

The present disclosure addresses the needs in patients with HFPEF as well as in patients at risk of developing HFPEF, due to conditions including but not limited to hypertension, diabetes, COPD, atrial fibrillation, or ischemic heart disease.

Fumaric acid esters (FAEs) are approved in Germany for the treatment of psoriasis, are being evaluated in the United States for the treatment of psoriasis and multiple sclerosis, and have been proposed for use in treating a number of immunological, autoimmune, and inflammatory diseases and conditions.

FAEs and other fumaric acid derivatives have been proposed for use in treating a wide-variety of diseases and conditions involving immunological, autoimmune, and/or inflammatory processes including psoriasis (Joshi and Strebel, WO 1999/49858; US. Pat. No. 6,277,882; Mrowietz and Asadullah, Trends Mol Med 2005, 111(1), 43-48; and Yazdi and Mrowietz, Clinics Dermatology 2008, 26, 522-526); asthma and chronic obstructive pulmonary diseases (Joshi et al., WO 2005/023241 and US 2007/0027076); mitochondrial and neurodegenerative diseases such as Parkinson's disease, Alzheimer's disease, Huntington's disease, retinopathia pigmentos, and mitochondrial encephalomyopathy (Joshi and Strebel, WO 2002/055063, US 2006/0205659, U.S. Pat. Nos. 6,509,376, 6,858,750, and 7,157,423); transplantation (Joshi and Strebel, WO 2002/055063, US 2006/0205659, U.S. Pat. Nos. 6,359,003, 6,509,376, and 7,157,423; and Lehmann et al., Arch Dermatol Res 2002, 294, 399-404); autoimmune diseases (Joshi and Strebel, WO 2002/055063, U.S. Pat. Nos. 6,509,376, 7,157,423, and US 2006/0205659) including multiple sclerosis (MS) (Joshi and Strebel, WO 1998/52549 and U.S. Pat. No. 6,436,992; Went and Lieberburg, US 2008/0089896; Schimrigk et al., Eur J Neurology 2006, 13, 604-610; and Schilling et al., Clin Experimental Immunology 2006, 145, 101-107); ischemia and reperfusion injury (Joshi et al., US 2007/0027076); AGE-induced genuine damage (Heidland, WO 2005/027899); inflammatory bowel diseases such as Crohn's disease and ulcerative colitis; arthritis; and others (Nilsson et al., WO 2006/037342 and Nilsson and Muller, WO 2007/042034).

FUMADERM®, an enteric coated tablet containing a salt mixture of monoethyl fumarate and dimethyl fumarate (DMF) which is rapidly hydrolyzed to monomethyl fumarate, regarded as the main bioactive metabolite, was approved in Germany in 1994 for the treatment of psoriasis. FUMA- DERM® is dosed three times daily (TID) with 1-2 grams/day administered for the treatment psoriasis. FUMADERM® exhibits a high degree of interpatient variability with respect to drug absorption, and food strongly reduces bioavailability. Absorption is thought to occur in the small intestine with peak levels achieved 5-6 hours after oral administration. Significant side effects occur in 70-90% of patients (Brewer and Rogers, Chu Expt'l Dermatology 2007, 32, 246-49; and Hoefnagel et al., Br J Dermatology 2003, 149, 363-369). Side effects of current FAE therapy include gastrointestinal upset including nausea, vomiting, diarrhea, and/or transient flushing of the skin.

Dimethyl fumarate (DMF) is the active component of BG-12, also known as Tecfidera®, studied for the treatment of relapsing-remitting MS (RRMS). In a Phase IIb RRMS study, BG-12 significantly reduced gadolinium-enhancing brain lesions. In preclinical studies, DMF administration has been shown to inhibit central nervous system (CNS) inflammation in murine and rat experimental autoimmune encephalomyelitis (EAE). It has also been found that DMF can inhibit astrogliosis and microglial activations associated with EAE. See, e.g., US Published Application No. 2012/0165404.

Despite its benefits, dimethyl fumarate is also associated with significant drawbacks. For example, dimethyl fumarate is known to cause side effects upon oral administration, such as flushing and gastrointestinal events including, nausea, diarrhea, and/or upper abdominal pain in subjects. See, e.g., Gold et al., N. Eng. J. Med., 2012, 367(12), 1098-1107. Dimethyl fumarate is dosed twice daily (BID) or TID with a total daily dose of about 480 mg to about 1 gram or more.

Further, in the use of a drug for long-term therapy, it is desirable that the drug be formulated so that it is suitable for once- or twice-daily administration to aid patient compliance. A dosing frequency of once-daily or less is even more desirable.

Another problem with long-term therapy is the requirement of determining an optimum dose, which can be tolerated by the patient. If such a dose is not determined, this can lead to a diminution in the effectiveness of the drug being administered.

Accordingly, it is an object of the present disclosure to provide compositions, which are suitable for long-term administration for patients in need of therapy of heart failure disease, including heart failure with preserved ejection fraction.

It is a further object of the present disclosure to provide the use of a pharmaceutically active agent in a manner which enables one to achieve a tolerable steady state level of the drug in a subject being treated therewith.

Because of the disadvantages of dimethyl fumarate described above, there continues to be a need to decrease the dosing frequency, reduce side-effects, and/or improve the physicochemical properties associated with DMF. There remains, therefore, a real need in the treatment of certain conditions for a product that retains the pharmacological advantages of DMF but overcomes its flaws in formulation and/or adverse effects upon administration. The present disclosure addresses these needs in patients with heart failure disease.

SUMMARY

The present disclosure relates to methods and compositions useful in the treatment of heart failure diseases. The methods and compositions described herein comprise one or more prodrugs (e.g., aminoalkyl prodrugs) of monomethyl fumarate (MMF) for the treatment of a heart failure disease. In some embodiments, heart failure disease is heart failure with preserved ejection fraction (HFPEF).

More specifically, the compounds of the disclosure can be converted in vivo, upon oral administration, to monomethyl fumarate. Upon conversion, the active moiety (i.e., monomethyl fumarate) is effective in treating subjects suffering from a heart failure disease.

Prodrugs of monomethyl fumarate refer to compounds described in U.S. Pat. No. 8,669,281, which is herein incorporated by reference in its entirety, having, in part, a compound of Formula (I), or a pharmaceutically acceptable salt, polymorph, hydrate, solvate or co-crystal thereof:

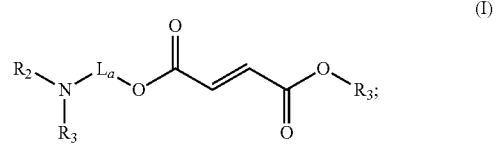

(I)

wherein:

$R_1$ is unsubstituted $C_1$-$C_6$ alkyl;

$L_a$ is substituted or unsubstituted $C_1$-$C_6$ alkyl linker, substituted or unsubstituted $C_3$-$C_{10}$ carbocycle, substituted or unsubstituted $C_6$-$C_{10}$ aryl, substituted or unsubstituted heterocycle comprising one or two 5- or 6-member rings and 1-4 heteroatoms selected from N, O and S, or substituted or unsubstituted heteroaryl comprising one or two 5- or 6-member rings and 1-4 heteroatoms selected from N, O and S; and $R_2$ and $R_3$ either:

(a) are each, independently, H, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_6$-$C_{10}$ aryl, substituted or unsubstituted $C_3$-$C_{10}$ carbocycle, substituted or unsubstituted heterocycle comprising one or two 5- or 6-member rings and 1-4 heteroatoms selected from N, O, and S, or substituted or unsubstituted heteroaryl comprising one or two 5- or 6-member rings and 1-4 heteroatoms selected from N, O, and S; or alternatively, (b) form, together with the nitrogen atom to which they are attached, a substituted or unsubstituted heteroaryl comprising one or two 5- or 6-member rings and 1-4 heteroatoms selected from N, O, and S or a substituted or unsubstituted heterocycle comprising one or two 5- or 6-member rings and 1-4 heteroatoms selected from N, O, and S.

In one embodiment of the present disclosure, one or more prodrugs of monomethyl fumarate comprise a compound having the formula:

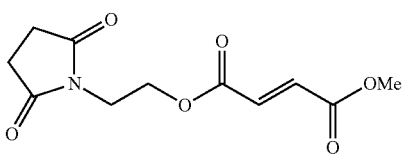 [SMILES: COC(=O)/C=C/C(=O)OCCN1C(=O)CCC1=O]

or a pharmaceutically acceptable salt thereof.

The present disclosure also provides pharmaceutical compositions comprising one or more compounds of any of the formulae described in U.S. Pat. No. 8,669,281, the disclosure of which is herein incorporated by reference in its entirety, and one or more pharmaceutically acceptable carriers for the treatment of heart failure disease. In some embodiments, the heart failure disease is heart failure with preserved ejection fraction (HFPEF).

In another embodiment a pharmaceutical preparation is administered to the patient, wherein said pharmaceutical composition comprises 210 mg to 1260 mg of a compound having the formula:

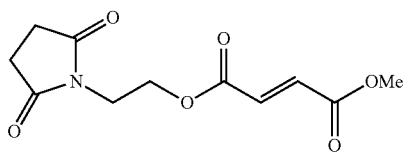 [SMILES: COC(=O)/C=C/C(=O)OCCN1C(=O)CCC1=O]

The present disclosure also provide methods of treating a heart failure disease by administering to a subject in need thereof, a therapeutically effective amount of a compound of any of the formulae described herein, or a pharmaceutically acceptable salt, polymorph, hydrate, solvate, or co-crystal thereof, such that the disease is treated.

The present disclosure also provides methods of treating heart failure with preserved ejection fraction (HFPEF) by administering to a subject in need thereof, a therapeutically effective amount of a compound of any of the formulae described herein, or a pharmaceutically acceptable salt, polymorph, hydrate, solvate, or co-crystal thereof such that the disease is treated.

The present disclosure also provides methods of reducing progression to heart failure in patients with hypertension by administering to a subject in need thereof, a therapeutically effective amount of a compound of any of the formulae described herein, or a pharmaceutically acceptable salt, polymorph, hydrate, solvate, or co-crystal thereof.

The present disclosure also provides compositions that enable improved oral, controlled- or sustained-release formulations for use in the treatment of heart failure disease. The compositions may enable formulations with a modified duration of therapeutic efficacy for reducing heart failure disease in subjects. For example, the compositions provide therapeutically effective amounts of monomethyl fumarate in subjects for at least about 8 hours, at least about 12 hours, at least about 16 hours, at least about 20 hours or at least about 24 hours.

In some embodiments, compositions comprise a therapeutically effective amount of one or more prodrugs of monomethyl fumarate that are shown to provide monomethyl fumarate plasma exposure comparable to dimethyl fumarate 120 mg to 720 mg per day.

In one embodiment, one or more prodrugs of monomethyl fumarate (MMF) are administered in combination with one or more second agents useful for treating heart failure. In various embodiments, the second agent is a diuretic, an ace-inhibitor, a beta-blocker, an angiotensin receptor blocker, isosorbide dinitrate, hydralazine, air angiotensin receptor-neprilysin inhibitor, an aldosterone antagonist, a PDE5 inhibitor, a statin, a neprilysin inhibitor, an aldosterone inhibitor, or an antitumor necrosis factor-alpha therapy. In one embodiment, the second agent is a statin.

In another embodiment, a pharmaceutical composition comprises (a) compound having the formula:

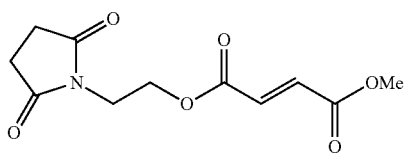 [SMILES: COC(=O)/C=C/C(=O)OCCN1C(=O)CCC1=O]

and (b) a statin and one or more pharmaceutically acceptable excipients.

In another embodiment, the pharmaceutical composition comprises a compound having the formula:

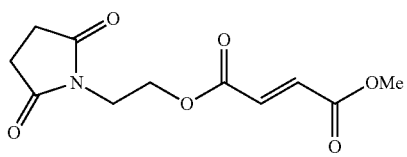 [SMILES: COC(=O)/C=C/C(=O)OCCN1C(=O)CCC1=O]

at a dose range of 210 mg to 1260 mg and a statin at a dose range of 10 mg to 80 mg.

Another aspect of the disclosure provides a method of treating a heart failure disease, in a subject in need thereof; the method comprising administering to the subject a therapeutically effective amount of (a) a compound having the formula;

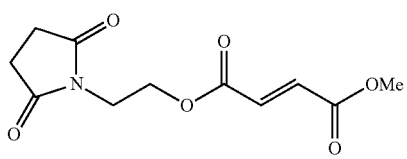 [SMILES: COC(=O)/C=C/C(=O)OCCN1C(=O)CCC1=O]

and either separately or together with (b) a statin. In some embodiment, the heart failure is heart failure with preserved ejection fraction.

The present disclosure also provides compositions and methods, which may result in decreased side effects upon administration to a subject relative to dimethyl fumarate. For example, gastric irritation and flushing are known side effects of oral administration of dimethyl fumarate in some subjects. The compositions and methods of the present disclosure can be utilized in subjects that have experienced or are at risk of developing such side effects.

The present disclosure also provides for compositions which exhibit improved physical stability relative to dimethyl fumarate. Specifically, dimethyl fumarate is known in the art to undergo sublimation at ambient and elevated temperature conditions. The compounds of the disclosure possess greater physical stability than dimethyl fumarate under controlled conditions of temperature and relative humidity. Specifically, in one embodiment, the compounds of the formulae described herein exhibit decreased sublimation relative to dimethyl fumarate.

Further, dimethyl fumarate is also known to be a contact irritant. In one embodiment, the compounds of the present disclosure exhibit reduced contact irritation relative to dimethyl fumarate. For example, the compounds of the formulae described herein exhibit reduced contact irritation relative to dimethyl fumarate.

The present disclosure also provides for compositions that exhibit decreased food effect relative to dimethyl fumarate. The bioavailability of dimethyl fumarate is known in the art to be reduced when administered with food. Specifically, in one embodiment, the compounds of the formulae described herein exhibit decreased food effect relative to dimethyl fumarate.

DETAILED DESCRIPTION

The foregoing is a summary, and thus, necessarily limited in detail. The above-mentioned aspects, as well as other aspects, features, and advantages of the present technology described below in connection with various embodiments, with reference made to the accompanying drawings.

Definitions

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include moieties having from one to six carbon atoms, such as, but not limited to, methyl, ethyl, n-propyl, i-propyl, n-butyl, s-butyl, t-butyl, n-pentyl, s-pentyl, or n-hexyl.

In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, "alkyl linker" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl linker is intended to include $C_1$, $C_2$, $C_3$, $C_4$, $C_5$ and $C_6$ alkyl linker groups. Examples of alkyl linker include, moieties having from one to six carbon atoms, such as, but not limited to, methyl (—$CH_2$—), ethyl (—$CH_2CH_2$—), n-propyl (—$CH_2CH_2CH_2$—), i-propyl (—$CHCH_3CH_2$—), n-butyl (—$CH_2CH_2CH_2CH_2$—), s-butyl (—$CHCH_3CH_2CH_2$—), i-butyl (—$C(CH_3)_2CH_2$—), n-pentyl (—$CH_2CH_2CH_2CH_2CH_2$—), s-pentyl (—$CHCH_3CH_2CH_2CH_2$—) or n-hexyl (—$CH_2CH_2CH_2CH_2CH_2CH_2$—). The term "substituted alkyl linker" refers to alkyl linkers having substituents replacing one or more hydrogen atoms on one or more carbons of the hydrocarbon backbone. Such substituents do not alter the sp3-hybridization of the carbon atom to which they are attached and include those listed below for "substituted alkyl."

"Heteroalkyl" groups are alkyl groups, as defined above, that have an oxygen, nitrogen, sulfur, or phosphorous atom replacing one or more hydrocarbon backbone carbon atoms.

As used herein, the term "cycloalkyl", "$C_3$, $C_4$, $C_5$, $C_6$, $C_7$ or $C_8$ cycloalkyl" or "$C_3$-$C_8$ cycloalkyl" is intended to include hydrocarbon rings having from three to eight carbon atoms in their ring structure. In one embodiment, a cycloalkyl group has five or six carbons in the ring structure.

The term "substituted alkyl" refers to alkyl moieties having substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl(benzyl)).

Unless the number of carbons is otherwise specified, "lower alkyl" includes an alkyl group, as defined above, having from one to six, or in another embodiment from one to four, carbon atoms in its backbone structure. "Lower alkenyl" and "lower alkynyl" have chain lengths of, for example, two to six or two to four carbon atoms.

"Aryl" includes groups with aromaticity, including "conjugated" or multicyclic, systems with at least one aromatic ring. Examples include phenyl, benzyl, naphthyl, etc.

"Heteroaryl" groups are aryl groups, as defined above, having from one to four heteroatoms in the ring structure, and may also be referred to as "aryl heterocycles" or "heteroaromatics". As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and S(O)$_p$, where p=1 or 2). It is to be noted that total number of S and O atoms in the heteroaryl is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricycle, bicyclic, e.g., naphthalene, benzoxazole, benzodioxazole, benzothiazole, benzoimidazole, benzothiophene, methylenedioxyphenyl, quinoline, isoquinoline, naphthrydine, indole, benzofuran, purine, benzofuran, deazapurine, or indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

The aryl or heteroaryl aromatic ring can be substituted at one or more ring positions with such substituents as described above, for example, alkyl, alkenyl, akynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

As used herein, "carbocycle" or "carbocyclic ring" is intended to include any stable monocyclic, bicyclic or tricyclic ring having the specified number of carbons, any of which may be saturated, unsaturated, or aromatic. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclo octane, [4.3.0]bicyclononane, [4.4.0]bicyclodecane and [2.2.2]bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

As used herein, "heterocycle" includes any ring structure (saturated or partially unsaturated) which contains at least one ring heteroatom (e.g., N, O or S). Examples of heterocycles include, but are not limited to, morpholine, pyrrolidine, tetrahydrothiophene, piperidine, piperazine and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2-H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "substituted", as used herein, means that any one or more hydrogen atoms on the designated atom is replaced with a selection from the indicated groups, provided that the designated atoms normal valency is not exceeded, and that the substitution results in a stable compound. When a substituent is keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

As used herein, a "subject in need thereof" is a subject having a heart failure disease. In one embodiment, a subject in need thereof has heart failure with preserved ejection fraction (HFPEF) or is at risk of developing HFPEF. A "subject" includes a mammal. The mammal can be e.g., any mammal, e.g., a human, primate, bird, mouse, rat, fowl, dog, cat, cow, horse, goat, camel, sheep or a pig. In one embodiment, the mammal is a human.

As used herein, "controlled-release" means a dosage form in which the release of the active agent is controlled or modified over a period of time. Controlled can mean, for example, sustained, delayed or pulsed-release at a particular time. For example, controlled-release can mean that the release of the active ingredient is extended for longer than it would be in an immediate-release dosage form, i.e., at least over several hours.

As used herein, "immediate-release" means a dosage form in which greater than or equal o about 75% of the active ingredient is released within two hours, or, more specifically, within one hour, of administration. Immediate-release or controlled-release may also be characterized by their dissolution profiles.

As used herein, "pharmacokinetic parameters" describe the in vivo characteristics of the active ingredient over time, including for example plasma concentration of the active ingredient. As used herein, "$C_{max}$" means the measured concentration of the active ingredient in the plasma at the point of maximum concentration. "$T_{max}$" refers to the time at which the concentration of the active ingredient in the plasma is the highest. "AUC" is the area under the curve of a graph of the concentration of the active ingredient (typically plasma concentration) vs. time, measured from one time to another.

As used herein, "therapeutically effective amount" means an amount required to reduce symptoms of the disease in an individual.

Compositions

The present disclosure provides methods of treating a heart failure disease by administering a compound herein of Formula (I), (Ia), (Ib), (II), or (III), and pharmaceutical compositions containing a compound of Formula (I), (Ia), (Ib), (II), or (III).

The present disclosure provides, in part, methods for the treatment of a heart failure disease by administering to a subject in need thereof, a therapeutically effective amount of a compound of Formula (I), (Ia), (Ib), (II), or (III), or a pharmaceutically acceptable salt, polymorph, hydrate, solvate, or co-crystal thereof.

In one embodiment, the heart failure disease may be heart failure with preserved ejection fraction (HFPEF); heart failure with ejection fraction ≥40%; diastolic heart failure; heart failure with elevated levels of TNF-α, IL-6, CRP, or TGF-β; hypertension with a risk of developing HFPEF; atrial fibrillation with a risk of developing HFPEF; diabetes with a risk of developing HFPEF; COPD with a risk of developing HFPEF; ischemic heart disease with a risk of developing HFPEF; obesity with a risk of developing HFPEF; chronic heart failure; compensated heart failure; decompensated heart failure; or other conditions known to have a high risk of developing HFPEF. In particular, heart failure disease is heart failure with preserved ejection fraction (HFPEF). The present disclosure further provides the use of a compound of Formula (I), (Ia), (Ib), (II), or (III), or a pharmaceutically acceptable salt, polymorph, hydrate, solvate, or co-crystal thereof, for the preparation of a medicament useful for the treatment of a heart failure disease.

In a further embodiment, the present disclosure provides methods for the treatment of a disease or a symptom of a disease described herein by administering to a subject in need thereof, a therapeutically effective amount of a compound of Formula (I), (Ia), (Ib), (II), or (III), or a pharmaceutically acceptable salt, polymorph, hydrate, solvate, or co-crystal thereof. The present disclosure further provides the use of a compound of Formula (I), (Ia), (Ib), (II), or (Ill), or a pharmaceutically acceptable salt, polymorph, hydrate, solvate, or co-crystal thereof, for the preparation of a medicament useful for the treatment of a disease or a symptom of a disease described herein.

In another embodiment, the present disclosure provides a method for the treatment of a heart failure disease by administering to a subject in need thereof, a therapeutically effective amount of a compound of Formula (I), or a pharmaceutically acceptable salt, polymorph, hydrate, solvate, or co-crystal thereof:

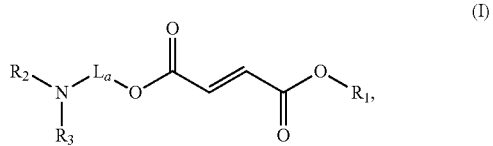

wherein:

$R_1$ is unsubstituted $C_1$-$C_6$ alkyl;

$L_a$ is substituted or unsubstituted $C_1$-$C_6$ alkyl linker, substituted or unsubstituted $C_3$-$C_{10}$ carbocycle, substituted or unsubstituted $C_6$-$C_{10}$ aryl, substituted or unsubstituted heterocycle comprising one or two 5- or 6-member rings and 1-4 heteroatoms selected from N, O, and S, or substituted or unsubstituted heteroaryl comprising one or two 5- or 6-member rings and 1-4 heteroatoms selected from N, O and S; and either:

$R_2$ and $R_3$ are either:

(a) each independently, H, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_6$-$C_{10}$ aryl, substituted or unsubstituted $C_3$-$C_{10}$ carbocycle, substituted or unsubstituted heterocycle comprising one or two 5- or 6-member rings and 1-4 heteroatoms selected from N, O and S, or substituted or unsubstituted heteroaryl comprising one or two 5- or 6-member rings and 1-4 heteroatoms selected from N, O, and S; or alternatively.

(b) form, together with the nitrogen atom to which they are attached, a substituted or unsubstituted heteroaryl comprising one or two 5- or 6-member rings and 1-4 heteroatoms selected from N, O, and S or a substituted or unsubstituted heterocycle comprising one or two 5- or 6-member rings and 1-4 heteroatoms selected from N, O, and S.

For example, the heart failure disease is HFPEF.

For example, the heart failure disease is heart failure with an ejection fraction ≥40%.

For example, the heart failure disease is diastolic heart failure.

For example, the heart failure disease is heart failure with elevated levels of TNF-α, IL-6, CRP, or TGF-β.

For example, the heart failure disease is hypertension with a risk of developing HFPEF.

For example, the heart failure disease is atrial fibrillation with a risk of developing HFPEF.

For example, the heart failure disease is diabetes with a risk of developing

For example, the heart failure disease is COPD with a risk of developing HFPEF.

For example, the heart failure disease is ischemic heart disease with a risk of developing HFPEF.

For example, the heart failure disease is obesity with a risk of developing HFPEF.

For example, the heart failure disease is chronic heart failure.

For example, the heart failure disease is compensated heart failure.

For example, the heart failure disease is decompensated heart failure.

For example, the heart failure disease is a condition that has a high risk of developing HFPEF.

For example, the compound of Formula (I) is a compound listed in Table 1.

For example, in the compound of Formula (I), $R_1$ is methyl.

For example, in the compound of Formula (I), $R_1$ is ethyl.

For example, in the compound of Formula (I) $L_a$ is substituted or unsubstituted $C_1$-$C_6$ alkyl linker.

For example, in the compound of Formula (I), $L_a$ is substituted or unsubstituted $C_1$-$C_3$ alkyl linker.

For example, in the compound of Formula (I), $L_a$ is substituted or unsubstituted $C_2$ alkyl linker.

For example, in the compound of Formula (I), $L_a$ is methyl substituted or unsubstituted $C_2$ alkyl linker.

For example, in the compound of Formula (I), $L_a$ is di-methyl substituted or unsubstituted $C_2$ alkyl linker.

For example, in the compound of Formula (I), $L_a$ is methyl or di-methyl substituted $C_2$ alkyl linker.

For example, in the compound of Formula (I), $L_a$ is unsubstituted $C_2$ alkyl linker.

For example, in the compound of Formula (I), $R_2$ is substituted or unsubstituted $C_1$-$C_6$ alkyl.

For example, in the compound of Formula (I), $R_2$ is unsubstituted $C_1$-$C_6$ alkyl.

For example, in the compound of Formula (I), $R_2$ is unsubstituted $C_1$-$C_3$ alkyl.

For example, in the compound of Formula (I), $R_2$ is unsubstituted $C_1$-$C_2$ alkyl.

For example, in the compound of Formula (I), $R_2$ is $C(O)OR_a$-substituted $C_1$-$C_6$ alkyl, wherein $R_a$ is H or unsubstituted $C_1$-$C_6$ alkyl.

For example, in the compound of Formula (I), $R_2$ is $S(O)(O)R_b$-substituted $C_1$-$C_6$ alkyl, wherein $R_b$ is unsubstituted $C_1$-$C_6$ alkyl.

For example, in the compound of Formula (I), $R_3$ is H.

For example, in the compound of Formula (I), $R_3$ is substituted or unsubstituted $C_1$-$C_6$ alkyl.

For example, in the compound of Formula (I), $R_3$ is unsubstituted $C_1$-$C_6$ alkyl.

For example, in the compound of Formula (I), $R_2$ and $R_3$, together with the nitrogen atom to which they are attached, form a substituted or unsubstituted heteroaryl comprising one or two 5- or 6-member rings and 1-4 heteroatoms selected from N, O, and S, or a substituted or unsubstituted heterocycle comprising one or two 5- or 6-member rings and 1-4 heteroatoms selected from N, O, and S.

For example, in the compound of Formula (I), $R_2$ and $R_3$, together with the nitrogen atom to which they are attached, form a substituted or unsubstituted heterocycle comprising one or two 5- or 6-member rings and 1-4 heteroatoms selected from N, O, and S.

For example, in the compound of Formula (I), $R_2$ and $R_3$, together with the nitrogen atom to which they are attached, form a substituted or unsubstituted pyrrolidinyl, imidazolidinyl, pyrazolidinyl, oxazolidinyl, isoxazolidinyl, triazolidinyl, tetrahydrofuranyl, piperidinyl, piperazinyl, or morpholinyl ring.

For example, in the compound of Formula (I), $R_2$ and $R_3$, together with the nitrogen atom to which they are attached, form a substituted or unsubstituted piperidinyl ring.

For example, in the compound of Formula (I), $R_2$ and $R_3$, together with the nitrogen atom to which they are attached, form an unsubstituted piperidinyl ring.

For example, in the compound of Formula (I), $R_2$ and $R_3$, together with the nitrogen atom to which they are attached, form a halogen substituted piperidinyl ring.

For example, in the compound of Formula (I), $R_2$ and $R_3$, together with the nitrogen atom to which they are attached, form a 4-halogen substituted piperidinyl ring.

For example, in the compound of Formula (I), $R_2$ and $R_3$, together with the nitrogen atom to which they are attached, form an unsubstituted morpholinyl ring.

For example, in the compound of Formula (I), $R_2$ and $R_3$, together with the nitrogen atom to which they are attached, form an unsubstituted pyrrolidinyl ring.

For example, in the compound of Formula (I), $R_2$ and $R_3$, together with the nitrogen atom to which they are attached, form a substituted or unsubstituted heteroaryl comprising one or two 5 or 6-member rings and 1-4 heteroatoms selected from N, O, and S.

For example, in the compound of Formula (I), $R_2$ is substituted or unsubstituted $C_6$-$C_{10}$ aryl.

For example, in the compound of Formula (I), $R_2$ is unsubstituted $C_6$-$C_{10}$ aryl.

For example, in the compound of Formula (I), $R_2$ is unsubstituted phenyl.

For example, in the compound of Formula (I), $R_2$ is unsubstituted benzyl.

In another embodiment, the present disclosure provides a method for the treatment of a heart failure disease by administering to a subject in need thereof a therapeutically effective amount of a compound of Formula (Ia), or a pharmaceutically acceptable salt, polymorph, hydrate, solvate, or co-crystal thereof:

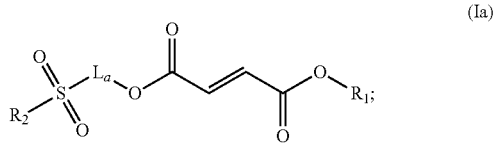

(Ia)

wherein:

$R_1$ is unsubstituted $C_1$-$C_6$ alkyl;

$L_a$ is substituted or unsubstituted $C_1$-$C_6$ alkyl linker, substituted or unsubstituted $C_3$-$C_{10}$ carbocycle, substituted or unsubstituted $C_6$-$C_{10}$ aryl, substituted or unsubstituted heterocycle comprising one or two 5- or 6-member rings and 1-4 heteroatoms selected from N, O, and S, or substituted or unsubstituted heteroaryl comprising one or two 5- or 6-member rings and 1-4 heteroatoms selected from N, O, and S; and $R_2$ is H, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_6$-$C_{10}$ aryl, substituted or unsubstituted $C_3$-$C_{10}$ carbocycle, substituted or unsubstituted heterocycle comprising one or two 5- or 6-member rings and 1-4 heteroatoms selected from N, O, and S, or substituted or unsubstituted heteroaryl comprising one or two 5- or 6-member rings and 1-4 heteroatoms selected from N, O, and S.

For example, the heart failure disease is HFPEF.

For example, the heart failure disease is heart failure with an ejection fraction ≥40%.

For example, the heart failure disease is diastolic heart failure.

For example, the heart failure is heart failure with elevated levels of TNF-α, IL-6, CRP, or TGF-β.

For example, the heart failure disease is hypertension with a risk of developing HFPEF.

For example, the heart failure disease is atrial fibrillation with a risk of developing HFPEF.

For example, the heart failure disease is diabetes with a risk of developing HFPEF.

For example, the heart failure disease is COPD with a risk of developing HFPEF.

For example, the heart failure disease is ischemic heart disease with a risk of developing HFPEF.

For example, the heart failure disease is obesity with a risk of developing HFPEF.

For example, the heart failure disease is chronic heart failure.

For example, the heart failure disease is compensated heart failure.

For example, the heart failure disease is decompensated heart failure.

For example, the heart failure disease is a condition that has a high risk of developing HFPEF.

For example, in the compound of Formula (Ia), $R_1$ is methyl.

For example, in the compound of Formula (Ia), $R_1$ is ethyl.

For example, in the compound of Formula (Ia), $L_a$ is substituted or unsubstituted $C_1$-$C_6$ alkyl linker.

For example, in the compound of Formula (Ia), $L_a$ is substituted or unsubstituted $C_1$-$C_3$ alkyl linker.

For example, in the compound of Formula (Ia), $L_a$ is substituted or unsubstituted $C_2$ alkyl linker.

For example, in the compound of Formula (Ia), $L_a$ is methyl substituted or unsubstituted $C_2$ alkyl linker.

For example, in the compound of Formula (Ia), $L_a$ is di-methyl substituted or unsubstituted $C_2$ alkyl linker.

For example, in the compound of Formula (Ia), $L_a$ is methyl or di-methyl substituted $C_2$ alkyl linker.

For example, in the compound of Formula (Ia), $L_a$ is unsubstituted $C_2$ alkyl linker.

For example, in the compound of Formula (Ia), $R_2$ is substituted or unsubstituted $C_1$-$C_6$ alkyl.

For example, in the compound of Formula (Ia), $R_2$ is unsubstituted $C_1$-$C_6$ alkyl.

For example, in the compound of Formula (Ia), $R_2$ is methyl.

For example, in the compound of Formula (Ia), $R_2$ is unsubstituted $C_1$-$C_3$ alkyl.

For example, in the compound of Formula (Ia), $R_2$ is unsubstituted $C_1$-$C_2$ alkyl.

For example, in the compound of Formula (Ia), $R_2$ is C(O)OR$_a$-substituted $C_1$-$C_6$ alkyl, wherein $R_a$ is H or unsubstituted $C_1$-$C_6$ alkyl.

For example, in the compound of Formula (Ia), R$_2$ is S(O)(O)R$_b$-substituted C$_1$-C$_6$ alkyl, wherein R$_b$ is unsubstituted C$_1$-C$_6$ alkyl.

In another embodiment, the present disclosure provides a method for the treatment of a heart failure disease by administering to a subject in need thereof a therapeutically effective amount of a compound of Formula (Ib), or a pharmaceutically acceptable polymorph, hydrate, solvate, or co-crystal thereof:

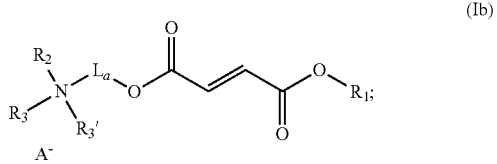

(Ib)

A$^-$ is a pharmaceutically acceptable anion;

R$_1$ is unsubstituted C$_1$-C$_6$ alkyl;

L$_a$ is substituted or unsubstituted C$_1$-C$_6$ alkyl linker, substituted or unsubstituted C$_3$-C$_{10}$ carbocycle, substituted or unsubstituted C$_6$-C$_{10}$ aryl, substituted or unsubstituted heterocycle comprising one or two 5- or 6-member rings and 1-4 heteroatoms selected from N, O, and S, or substituted or unsubstituted heteroaryl comprising one or two 5- or 6-member rings and 1-4 heteroatoms selected from N, O, and S;

R$_3$' is substituted or unsubstituted C$_1$-C$_6$ alkyl; and either:

(a) R$_2$ and R$_3$ are each, independently, H, substituted or unsubstituted C$_1$-C$_6$ alkyl, substituted or unsubstituted C$_2$-C$_6$ alkenyl, substituted or unsubstituted C$_2$-C$_6$ alkynyl, substituted or unsubstituted C$_6$-C$_{10}$ aryl, substituted or unsubstituted C$_3$-C$_{10}$ carbocycle, substituted or unsubstituted heterocycle comprising one or two 5- or 6-member rings and 1-4 heteroatoms selected from N, O, and S, or substituted or unsubstituted heteroaryl comprising one or two 5- or 6-member rings and 1-4 heteroatoms selected from N, O, and S; or alternatively, (b) R$_2$ and R$_3$, together with the nitrogen atom to which they are attached, form a substituted or unsubstituted heteroaryl comprising one or two 5- or 6-member rings and 1-4 heteroatoms selected from N, O, and S, or a substituted or unsubstituted heterocycle comprising one or two 5- or 6-member rings and 1-4 heteroatoms selected from N, O, and S.

For example, the heart failure disease is HFPEF.

For example, the heart failure disease is heart failure with an ejection fraction ≥40%.

For example, the heart failure disease is diastolic heart failure.

For example, the heart failure disease is heart failure with elevated levels of TNF-α, IL-6, CRP, or TGF-β.

For example, the heart failure disease is hypertension with a risk of developing HFPEF.

For example, the heart failure disease is atrial fibrillation with a risk of developing HFPEF.

For example, the heart failure disease is diabetes with a risk of developing HFPEF.

For example, the heart failure disease is COPD with a risk of developing HFPEF.

For example, the heart failure disease is ischemic heart disease with a risk of developing HFPEF.

For example, the heart failure disease is obesity with a risk of developing HFPEF.

For example, the heart failure disease is chronic heart failure.

For example, the heart failure disease is compensated heart failure.

For example, the heart failure disease is decompensated heart failure.

For example, the heart failure disease is a condition that has a high risk of developing HFPEF.

For example, in the compound of Formula (Ib), R$_1$ is methyl.

For example, in the compound of Formula (Ib), R$_1$ is ethyl.

For example, in the compound of Formula (Ib), L$_a$ is substituted or unsubstituted C$_1$-C$_6$ alkyl linker.

For example, in the compound of Formula (Ib), L$_a$ is substituted or unsubstituted C$_1$-C$_3$ alkyl.

For example, in the compound of Formula (Ib), L$_a$ is substituted or unsubstituted C$_2$ alkyl linker.

For example, in the compound of Formula (Ib), L$_a$ is methyl substituted or unsubstituted C$_2$ alkyl linker.

For example, in the compound of Formula (Ib), L$_a$ is di-methyl substituted or unsubstituted C$_2$ alkyl linker.

For example, in the compound of Formula (Ib), L$_a$ is methyl or di-methyl substituted C$_2$ alkyl linker.

For example, in the compound of Formula (Ib), L$_a$ is unsubstituted C$_2$ alkyl linker.

For example, in the compound of Formula (Ib), R$_2$ is substituted or unsubstituted C$_1$-C$_6$ alkyl.

For example, in the compound of Formula (Ib), R$_2$ is unsubstituted C$_1$-C$_6$ alkyl.

For example, in the compound of Formula (Ib), R$_2$ is unsubstituted C$_1$-C$_3$ alkyl.

For example, in the compound of Formula (Ib), R$_2$ is unsubstituted C$_1$-C$_2$ alkyl.

For example, in the compound of Formula (Ib), R$_2$ is C(O)OR$_a$-substituted C$_1$-C$_6$ alkyl, wherein R$_a$ is H or unsubstituted C$_1$-C$_6$ alkyl.

For example, in the compound of Formula (Ib), R$_2$ is S(O)(O)R$_b$-substituted C$_1$-C$_6$ alkyl, wherein R$_b$ is unsubstituted C$_1$-C$_6$ alkyl.

For example, in the compound of Formula (Ib), R$_3$ is H.

For example, in the compound of Formula (Ib), R$_3$ is substituted or unsubstituted C$_1$-C$_6$ alkyl.

For example, in the compound of Formula (Ib), R$_3$ is unsubstituted

For example, in the compound of Formula (Ib), R$_2$ and R$_3$, together with the nitrogen atom to which they are attached, form a substituted or unsubstituted heteroaryl comprising one or two 5- or 6-member rings and 1-4 heteroatoms selected from N, O, and S, or a substituted or unsubstituted heterocycle comprising one or two 5- or 6-member rings and 1-4 heteroatoms selected from N, O, and S.

For example, in the compound of Formula (Ib), R$_2$ and R$_3$, together with the nitrogen atom to which they are attached, form a substituted or unsubstituted heterocycle comprising one or two 5- or 6-member rings and 1-4 heteroatoms selected from N, O, and S.

For example, in the compound of Formula (Ib), R$_2$ and R$_3$, together with the nitrogen atom to which they are attached, form a substituted or unsubstituted pyrrolidinyl, imidazolidinyl, pyrazolidinyl, oxazolidinyl, isoxazolidinyl, triazolidinyl, tetrahydrofuranyl, piperidinyl, piperazinyl, or morpholinyl ring.

For example, in the compound of Formula (Ib), R$_2$ and R$_3$, together with the nitrogen atom to which they are attached, form a substituted or unsubstituted piperidinyl ring.

For example, in the compound of Formula (Ib), $R_2$ and $R_3$, together with the nitrogen atom to which they are attached, form an unsubstituted piperidinyl ring.

For example, in the compound of Formula (Ib), $R_2$ and $R_3$, together with the nitrogen atom to which they are attached, form a halogen substituted piperidinyl ring.

For example, in the compound of Formula (Ib), $R_2$ and $R_3$, together with the nitrogen atom to which they are attached, form a 4-halogen substituted piperidinyl ring.

For example, in the compound of Formula (Ib), $R_2$ and $R_3$, together with the nitrogen atom to which they are attached, form an unsubstituted morpholinyl ring.

For example, in the compound of Formula (Ib), $R_2$ and $R_3$, together with the nitrogen atom to which they are attached, form an unsubstituted pyrrolidinyl ring.

For example, in the compound of Formula (Ib), $R_2$ and $R_3$, together with the nitrogen atom to which they are attached, form a substituted or unsubstituted heteroaryl comprising one or two 5- or 6-member rings and 1-4 heteroatoms selected from N, O, and S.

For example, in the compound of Formula (Ib), $R_2$ is substituted or unsubstituted $C_6$-$C_{10}$ aryl.

For example, in the compound of Formula (Ib), $R_2$ is unsubstituted $C_6$-$C_{10}$ aryl.

For example, in the compound of Formula (Ib), $R_2$ is unsubstituted phenyl.

For example, in the compound of Formula (Ib), $R_2$ is unsubstituted benzyl.

For example, in the compound of Formula (Ib), $R_3'$ is unsubstituted $C_1$-$C_6$ alkyl.

For example, in the compound of Formula (Ib), $R_3'$ is unsubstituted $C_1$-$C_3$ alkyl For example, in the compound of Formula (Ib), $R_3'$ is methyl.

In one embodiment, the present disclosure a method for the treatment of a heart failure disease by administering to a subject in need thereof a therapeutically effective amount of a compound of Formula (II), or a pharmaceutically acceptable salt, polymorph, hydrate, solvate, or co-crystal thereof:

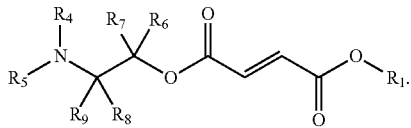

(II)

wherein:

$R_1$ is unsubstituted $C_1$-$C_6$ alkyl;

$R_4$ and $R_5$ are each, independently, H, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_6$-$C_{10}$ aryl, substituted or unsubstituted $C_1$-$C_{10}$ carbocycle, substituted or unsubstituted heterocycle comprising one or two 5- or 6-member rings and 1-4 heteroatoms selected from N, O, and S, or substituted or unsubstituted heteroaryl comprising one or two 5- or 6-member rings and 1-4 heteroatoms selected from N, O, and S;

$R_6$, $R_7$, $R_8$ and $R_9$ are each, independently, H, substituted or unsubstituted $C_1$-$C_6$ alkyl, substituted or unsubstituted $C_2$-$C_6$ alkenyl, substituted or unsubstituted $C_2$-$C_6$ alkynyl or $C(O)OR_a$; and $R_a$ is H or substituted or unsubstituted $C_1$-$C_6$ alkyl.

For example, the heart failure disease is HFPEF.

For example, the heart failure disease is heart failure with an ejection fraction ≥40%.

For example, the heart failure disease is diastolic heart failure.

For example, the heart failure disease is heart failure with elevated levels of TNF-α, IL-6, CRP, or TGF-β.

For example, the heart failure disease is hypertension with a risk of developing HFPEF.

For example, the heart failure disease is atrial fibrillation with a risk of developing HFPEF.

For example, the heart failure disease is diabetes with a risk of developing HFPEF.

For example, the heart failure disease is COPD with a risk of developing HFPEF.

For example, the heart failure disease is ischemic heart disease with a risk of developing HFPEF.

For example, the heart failure disease is obesity with a risk of developing HFPEF.

For example, the heart failure disease is chronic heart failure.

For example, the heart failure disease is compensated heart failure.

For example, the heart failure disease is decompensated heart failure.

For example, the heart failure disease is a condition that has a high risk of developing HFPEF.

For example, in the compound of Formula (II), $R_1$ is methyl.

For example, in the compound of Formula(II), $R_1$ is ethyl.

For example, in the compound of Formula (II), $R_4$ is substituted or unsubstituted $C_1$-$C_6$ alkyl.

For example, in the compound of Formula (II), $R_4$ is unsubstituted $C_1$-$C_6$ alkyl.

For example, in the compound of Formula (II), $R_4$ is unsubstituted $C_1$-$C_3$ alkyl.

For example, in the compound of Formula (II), $R_4$ is unsubstituted $C_1$-$C_2$ alkyl.

For example, in the compound of Formula (II), $R_4$ is $C(O)OR_a$-substituted $C_1$-$C_6$ alkyl, wherein $R_a$ is H or unsubstituted $C_1$-$C_6$ alkyl.

For example, in the compound of Formula (II), $R_4$ is $S(O)(O)R_b$-substituted $C_1$-$C_6$ alkyl, wherein $R_b$ is unsubstituted $C_1$-$C_6$ alkyl.

For example, in the compound of Formula (II), $R_5$ is H.

For example, in the compound of Formula (II), $R_5$ is substituted or unsubstituted $C_1$-$C_6$ alkyl.

For example, in the compound of Formula (II), $R_5$ is unsubstituted $C_1$-$C_6$ alkyl.

For example, in the compound of Formula (II), $R_4$ is substituted or unsubstituted $C_6$-$C_{10}$ aryl.

For example, in the compound of Formula (II), $R_4$ is unsubstituted $C_6$-$C_{10}$ aryl.

For example, in the compound of Formula (II), $R_4$ is unsubstituted phenyl.

For example, in the compound of Formula (II), $R_4$ is unsubstituted benzyl.

For example, in the compound of Formula (II), $R_6$, $R_7$, $R_8$ and $R_9$ are each H.

For example, in the compound of Formula (II), $R_6$ is substituted or unsubstituted $C_1$-$C_6$ alkyl and $R_7$, $R_8$ and $R_9$ are each H.

For example, in the compound of Formula (II), $R_6$ is unsubstituted $C_1$-$C_6$ alkyl and $R_7$, $R_8$ and $R_9$ are each H.

For example, in the compound of Formula (II), $R_8$ is substituted or unsubstituted $C_1$-$C_6$ alkyl and $R_6$, $R_7$ and $R_9$ are each H.

For example, in the compound of Formula (II), $R_8$ is unsubstituted $C_1$-$C_6$ alkyl and $R_6$, $R_7$ and $R_9$ are each H.

For example, in the compound of Formula (II), $R_6$ and $R_8$ are each, independently, substituted or unsubstituted $C_1$-$C_6$ alkyl and $R_7$ and $R_9$ are each H.

For example, in the compound of Formula (II), $R_6$ and $R_8$ are each, independently, unsubstituted $C_1$-$C_6$ alkyl and $R_7$ and $R_9$ are each H.

For example, in the compound of Formula (II), $R_6$ and $R_7$ are each, independently, substituted or unsubstituted $C_1$-$C_6$ alkyl and $R_8$ and $R_9$ are each H.

For example, in the compound of Formula (II), $R_6$ and $R_7$ are each, independently, unsubstituted $C_1$-$C_6$ alkyl and $R_8$ and $R_9$ are each H.

For example, in the compound of Formula (II), $R_8$ and $R_9$ are each, independently, substituted or unsubstituted $C_1$-$C_6$ alkyl and $R_6$ and $R_7$ are each H.

For example, in the compound of Formula (II), $R_8$ and $R_9$ are each, independently, unsubstituted $C_1$-$C_6$ alkyl and $R_6$ and $R_7$ are each H.

In one embodiment, the present disclosure provides a method for the treatment of a heart failure disease by administering to a subject in need thereof a therapeutically effective amount of a compound of Formula (III), or a pharmaceutically acceptable salt, polymorph, hydrate, solvate, or co-crystal thereof:

(III)

wherein:
$R_1$ is unsubstituted $C_1$-$C_6$ alkyl;

is selected from the group consisting of:

X is N, O, S, or $SO_2$;
Z is C or N;
m is 0, 1, 2, or 3;
n is 1 or 2;
w is 0, 1, 2, or 3;
t is 0, 1, 2, 3, 4, 5, 6, 7, 8, 9, or 10;
$R_6$, $R_7$, $R_8$ and $R_9$ are each, independently, H, substituted or unsubstituted $C_1$-$C_6$ alkyl, substituted or unsubstituted $C_1$-$C_6$ alkenyl, substituted or unsubstituted $C_2$-$C_6$ alkynyl or $C(O)OR_a$; and $R_a$ is H or substituted or unsubstituted $C_1$-$C_6$ alkyl; and either:

(a) each $R_{10}$ is, independently, H, halogen, substituted or unsubstituted $C_1$-$C_6$ alkyl, substituted or unsubstituted $C_2$-$C_6$ alkenyl, substituted or unsubstituted $C_2$-$C_6$ alkynyl substituted or unsubstituted $C_3$-$C_{10}$ carbocycle, substituted or unsubstituted heterocycle comprising one or two 5- or 6-member rings and 1-4 heteroatoms selected from N, O, and S, or substituted or unsubstituted heteroaryl comprising one or two 5- or 6-member rings and 1-4 heteroatoms selected from N, O, and S; or alternatively (b) two $R_{10}$'s attached to the same carbon atom, together with the carbon atom to which they are attached, form a carbonyl, substituted or unsubstituted $C_3$-$C_{10}$ carbocycle, substituted or unsubstituted heterocycle comprising one or two 5- or 6-member rings and 1-4 heteroatoms selected from N, O, and S, or substituted or unsubstituted heteroaryl comprising one or two 5- or 6-member rings and 1-4 heteroatoms selected from N, O, and S; or alternatively (c) two $R_{10}$'s attached to different atoms, together with the atoms to which they are attached, form a substituted or unsubstituted $C_3$-$C_{10}$ carbocycle, substituted or unsubstituted heterocycle comprising one or two 5- or 6-member rings and 1-4 heteroatoms selected from N, O, and S, or substituted or unsubstituted heteroaryl comprising one or two 5- or 6-member rings and 1-4 heteroatoms selected from N, O, and S.

For example, the heart failure disease is HFPEF.

For example, the heart failure disease is heart failure with an ejection fraction ≥40%.

For example, the heart failure disease is diastolic heart failure.

For example, the heart failure is heart failure with elevated levels of TNF-α, IL-6, CRP, or TGF-β.

For example, the heart failure disease is hypertension with a risk of developing HFPEF.

For example, the heart failure disease is atrial fibrillation with a risk of developing HFPEF.

For example, the heart failure disease is diabetes with a risk of developing HFPEF.

For example, the heart failure disease is COPD with a risk of developing HFPEF.

For example, the heart failure disease is ischemic heart disease with a risk of developing HFPEF.

For example, the heart failure disease is obesity with a risk of developing HFPEF.

For example, the heart failure disease is chronic heart failure.

For example, the heart failure disease is compensated heart failure.

For example, the heart failure disease is decompensated heart failure.

For example, the heart failure disease is a condition that has a high risk of developing HFPEF.

For example, in the compound of Formula (III), $R_1$ is methyl.

For example, in the compound of Formula (III), $R_1$ is ethyl.

For example, in the compound of Formula (III), is

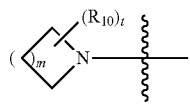

For example, in the compound of Formula (III),

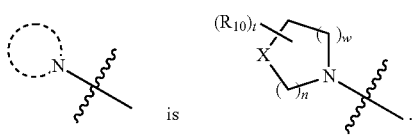

is

For example, in the compound of Formula (III),

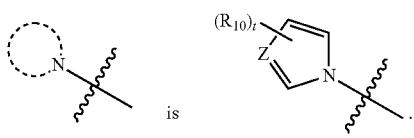

is

For example, in the compound of Formula (III),

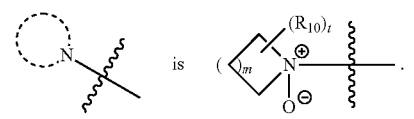

For example, in the compound of Formula (III), $R_6$ is substituted or unsubstituted $C_1$-$C_6$ alkyl and $R_7$, $R_8$ and $R_9$ are each H.

For example, in the compound of Formula (III), $R_6$ is unsubstituted $C_1$-$C_6$ alkyl and $R_7$, $R_8$ and $R_9$ are each H.

For example, in the compound of Formula (III), $R_8$ is substituted or unsubstituted $C_1$-$C_6$ alkyl and $R_6$, $R_7$ and $R_9$ are each H.

For example, in the compound of Formula (III), $R_8$ is unsubstituted $C_1$-$C_6$ alkyl and $R_6$, $R_7$ and $R_9$ are each H.

For example, in the compound of Formula (III), $R_6$ and $R_8$ are each, independently, substituted or unsubstituted $C_1$-$C_6$ alkyl and $R_7$ and $R_9$ are each H.

For example, in the compound of Formula (III), $R_6$ and $R_8$ are each, independently, unsubstituted $C_1$-$C_6$ alkyl and $R_7$ and $R_9$ are each H.

For example, in the compound of Formula (III), $R_6$ and $R_7$ are each, independently, substituted or unsubstituted $C_1$-$C_6$ alkyl and $R_8$ and $R_9$ are each H.

For example, in the compound of Formula (III), $R_6$ and $R_7$ are each, independently, unsubstituted $C_1$-$C_6$ alkyl and $R_8$ and $R_9$ are each H.

For example, in the compound of Formula (III), $R_8$ and $R_9$ are each, independently, substituted or unsubstituted $C_1$-$C_6$ alkyl and $R_6$ and $R_7$ are each H.

For example, in the compound of Formula (III), $R_8$ and $R_9$ are each, independently, unsubstituted $C_1$-$C_6$ alkyl and $R_6$ and $R_7$ are each H.

For example, the compound is a compound listed in Table 1

Representative compounds includes compounds listed in Table 1.

TABLE 1

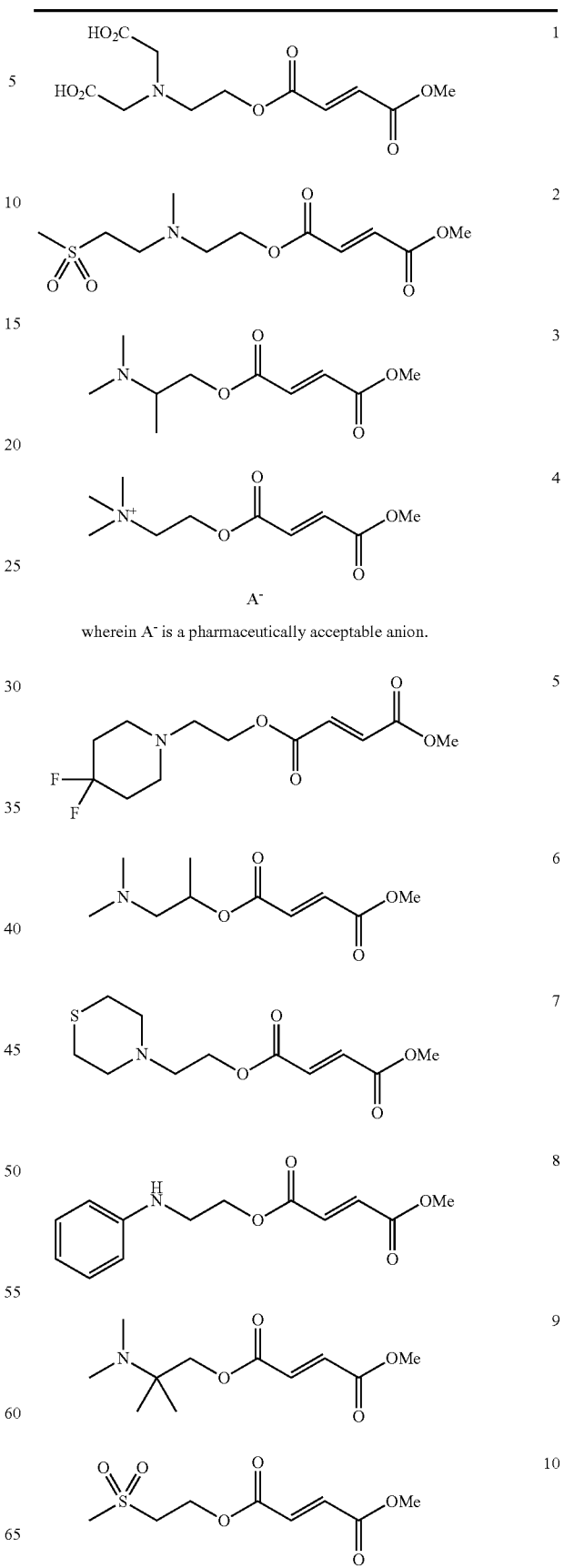

wherein A⁻ is a pharmaceutically acceptable anion.

TABLE 1-continued

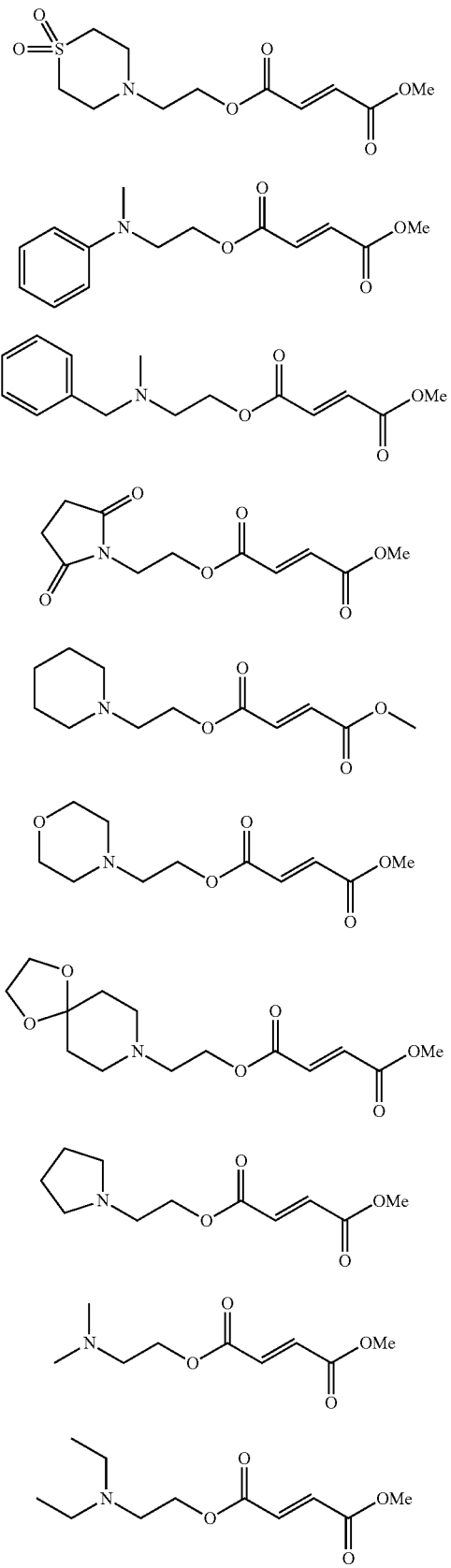

Dosage and Administration

The present disclosure also provides pharmaceutical compositions comprising one or more compounds of Formula (I), (Ia), (Ib), (II), or (III) and one or more pharmaceutically acceptable carriers for use in therapy of a heart failure disease, including heart failure with preserved ejection fraction.

In one embodiment, the pharmaceutical composition is a controlled release composition comprising a compound of Formula (I), (Ia), (Ib), (II), or (III) and one or more pharmaceutically acceptable carriers, wherein the controlled release composition provides a therapeutically effective amount of monomethyl fumarate to a subject. In another embodiment, the pharmaceutical composition is a controlled release composition comprising a compound of Formula (I), (Ia), (Ib), (II), or (III) and one or more pharmaceutically acceptable carriers, wherein the controlled release composition provides a therapeutically effective amount of monomethyl fumarate to a subject for at least about 8 hours to at least about 24 hours.

In another embodiment, the pharmaceutical composition is a controlled release composition comprising a compound of Formula (I), (Ia), (Ib), (II), or (III) and one or more pharmaceutically acceptable carriers, wherein the controlled release composition provides a therapeutically effective amount of monomethyl fumarate to a subject for at least about 8 hours, at least about 10 hours, at least about 12 hours, at least about 13 hours, at least about 14 hours, at least about 15 hours, at least about 16 hours, at least about 17 hours, at least about 18 hours, at least about 19 hours, at least about 20 hours, at least about 21 hours, at least about 22 hours, at least about 23 hours or at least about 24 hours or longer. For example, at least about 18 hours. For example, at least about 12 hours. For example, greater than 12 hours. For example, at least about 16 hours. For example, at least about 20 hours. For example, at least about 24 hours.

In another embodiment, a compound of Formula (I), (Ia), (Ib), (II), or (III) is efficiently converted to the active species, i.e., monomethyl fumarate, upon oral administration. For example, about 50 mole percent, about 55 mole percent, about 60 mole percent, about 65 mole percent, about 70 mole percent, about 75 mole percent, about 80 mole percent, about 85 mole percent, about 90 mole percent, or greater than 90 mole percent of the total dose of a compound of Formula (I), (Ia), (Ib), (II), or (III) administered is converted to monomethyl fumarate upon oral administration. In another embodiment, a compound of Formula (I), (Ia), (Ib), (II), or (III) is converted to the active species, i.e., monomethyl fumarate, upon oral administration more efficiently than dimethyl fumarate. In another embodiment, a compound of Formula (I), (Ia), (Ib), (II), or (III) is converted to the active species, i.e., monomethyl fumarate, upon oral administration more efficiently than one or more of the compounds described in U.S. Pat. No. 8,148,414, the disclosure of which is incorporated by reference in its entirety. For example, a compound of Formula (I), (Ia), (Ib), (II), or (III) is essentially completely converted to the active species, i.e., monomethyl fumarate, upon oral administration.

In another embodiment, any one of Compounds 1-20, as shown in Table 1, is efficiently converted to the active species, i.e., monomethyl fumarate, upon oral administration. For example, about 50 percent, about 55 percent, about 60 percent, about 65 percent, about 70 percent, about 75 percent, about 80 percent, about 85 percent, about 90 percent, or greater than 90 percent of the total dose of any one of Compounds 1-20 of Table 1 administered is converted to monomethyl fumarate upon oral administration. In another embodiment, any one of Compounds 1-20 of Table 1 is converted to the active species, i.e., monomethyl fumarate, upon oral administration more efficiently than dimethyl fumarate. In another embodiment, any one of Compounds 1-20 of Table 1 is converted to the active species, i.e., monomethyl fumarate, upon oral administration more efficiently than one or more of the compounds described in U.S. Pat. No. 8,148,414, the disclosure of which is herein incorporated by reference in its entirety. For example, any one of Compounds 1-20 of Table 1 is completely converted to the active species, i.e., monomethyl fumarate, upon oral administration.

For a drug to achieve its therapeutic effect, it is necessary to maintain the required level of blood or plasma concentration. Many drugs, including dimethyl fumarate, must be administered multiple times a day to maintain the required concentration. Furthermore, even with multiple administrations of such a drug per day, the blood or plasma concentrations of the active ingredient may still vary with time, i.e., at certain time points between administrations there are higher concentrations of the active ingredient than at other times. Thus, at certain time points of a 24-hour period, a patient may receive therapeutically effective amounts of the active ingredient, while at other time points the concentration of the active ingredient in the blood may fall below therapeutic levels. Additional problems with such drugs include that multiple dosing a day often adversely affects patient compliance with the treatment. Therefore, it is desirable to have a drug dosage form wherein the active ingredient is delivered in such a controlled manner that a constant or substantially constant level of blood or plasma concentration of the active ingredient can be achieved by one or at most two dosing per day. Accordingly, the present disclosure provides controlled-release formulations as described below. In general, such formulations are known to those skilled in the art or are available using conventional methods.

The controlled-release formulations provided herein provide desirable properties and advantages. For example, the formulations can be administered once daily, which is particularly desirable for the subjects described herein. The formulation can provide many therapeutic benefits that are not achieved with corresponding shorter acting or immediate-release preparations. For example, the formulation can maintain lower, more steady plasma peak values, for example, $C_{max}$, so as to reduce the incidence and severity of possible side effects.

Sustained-release dosage forms release their active ingredient into the gastro-intestinal tract of a patient over a sustained period of time following administration of the dosage form to the patient. Particular dosage forms include: (a) those in which the active ingredient is embedded in a matrix from which it is released by diffusion or erosion; (b) those in which the active ingredient is present in a core which is coated with a release rate-controlling membrane; (c) those in which the active ingredient is present in a core provided with an outer coating impermeable to the active ingredient, the outer coating having an aperture (which may be drilled) for release of the active ingredient; (d) those in which the active ingredient is released through a semipermeable membrane, allowing the drug to diffuse across the membrane or through liquid filled pores within the membrane; and (e) those in which the active ingredient is present as an ion exchange complex.

It will be apparent to those skilled in the art that some of the above means of achieving sustained-release may be combined, for example a matrix containing the active compound may be formed into a multiparticulate and/or coated with an impermeable coating provided with an aperture.

Pulsed-release formulations release the active compound after a sustained period of time following administration of the dosage form to the patient. The release may then be in the form of immediate- or sustained-release. This delay may be achieved by releasing the drug at particular points in the gastro-intestinal tract or by releasing drug after a predetermined time. Pulsed-release formulations may be in the form of tablets or multiparticulates or a combination of both. Particular dosage forms include: (a) osmotic potential triggered release (see U.S. Pat. No. 3,952,741); (b) compression coated two layer tablets (see U.S. Pat. No. 5,464,633); (c) capsules containing an erodible plug see U.S. Pat. No. 5,474,784); (d) sigmoidal releasing pellets (referred to in U.S. Pat. No. 5,112,621); and (e) formulations coated with or containing pH-dependent polymers including shellac, phthalate derivatives, polyacrylic acid derivatives, and crotonic acid copolymers.

Dual release formulations can combine the active ingredient in immediate release form with additional active ingredient in controlled-release form. For example, a bilayer tablet can be formed with one layer containing immediate release active ingredient and the other layer containing the active ingredient embedded in a matrix from which it is released by diffusion or erosion. Alternatively, one or more immediate release beads can be combined with one or more beads which are coated with a release rate-controlling membrane in a capsule to give a dual release formulation. Sustained release formulations in which the active ingredient is present in core provided with an outer coating impermeable to the active ingredient, the outer coating having an aperture (which may be drilled) for release of the active ingredient, can be coated with drug in immediate release form to give a dual release formulation. Dual release formulations can also combine drug in immediate release form with additional drug in pulsed release form. For example, a capsule containing an erodible plug could liberate drug initially and, after a predetermined period of time, release additional drug in immediate- or sustained-release form.

In some embodiments, the dosage forms to be used can be provided as controlled-release with respect to one or more active ingredients therein using, for example, hydroxypropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the pharmaceutical compositions of the disclosure. Thus, single unit dosage forms suitable for oral administration, such as tablets, capsules, gelcaps, and caplets that are adapted for controlled-release are encompassed by the present disclosure.

Most controlled-release formulations are designed to initially release an amount of drug that promptly produces the desired therapeutic effect and gradually and continually release additional amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, concentration, or other physiological conditions or compounds.

Powdered and granular formulations of a pharmaceutical preparation of the disclosure may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of a dispersing agent, wetting agent, suspending agent, and a preservative. Additional excipients, such as fillers, sweeteners, flavoring, or coloring agents, may also be included in these formulations.

A formulation of a pharmaceutical composition of the disclosure suitable for oral administration may be prepared or packaged in the form of a discrete solid dose unit including, but not limited to, a tablet, a hard or soft capsule, a cachet, a troche, or a lozenge, each containing a predetermined amount of the active ingredient. In one embodiment, a formulation of a pharmaceutical composition of the disclosure suitable for oral administration is coated with an enteric coating.

A tablet comprising the active ingredient may, for example, be made by compressing or molding the active ingredient, optionally with one or more additional ingredients. Compressed tablets may be prepared by compressing, in a suitable device, the active ingredient in a free flowing form such as a powder or granular preparation, optionally mixed with one or more of a binder, a lubricant, an excipient, a surface-active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate and poloxamers. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may he coated using methods described in U.S. Pat. Nos. 4,256,108; 4,160,452; and 4,265,874, the disclosure of which are each herein incorporated by reference in their entireties, to form osmotically-controlled release tablets, optionally, with laser drilling. Tablets may further comprise a sweetener, a flavoring agent, a coloring agent, a preservative, or some combination of these in order to provide for pharmaceutically elegant and palatable formulations.

Hard capsules comprising the active ingredient may be made using a physiologically degradable composition, such as gelatin or HPMC. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

The dose will be adjusted to the individual requirements in each particular case. That dosage may vary within wide limits depending upon numerous factors such as the severity of the disease to be treated, the age and general health condition of the patient, other medicaments with which the patient is being treated, the route and form of administration, and the preferences and experience of the medical practitioner involved. For oral administration, therapeutically effective amount of one or more prodrug of monomethyl fumarate that is shown to provide MMF plasma exposure comparable to 120 mg to 720 mg per day of dimethyl fumarate (DMF) as a monotherapy and/or in combination therapy. In one embodiment, daily dose comprises 210 mg to 1260 mg of the compound having the formula:

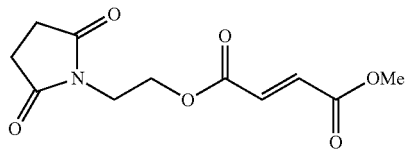 [SMILES: COC(=O)/C=C/C(=O)OCCN1C(=O)CCC1=O]

In another embodiment, the daily dose would be 420 mg BID, with the upper limit being 420 mg TID of the compound having the formula

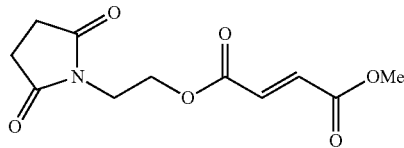 [SMILES: COC(=O)/C=C/C(=O)OCCN1C(=O)CCC1=O]

One of ordinary skill in treating diseases described herein will be able, without undue experimentation and in reliance on personal knowledge, experience and the disclosures of this application, to ascertain a therapeutically effective amount of the compounds of the present invention for a given disease and patient.

According to the present disclosure, administration of one or more prodrug of monomethyl fumarate may also be carried out in the combination with administration of one or more preparations of a second agent useful for treating heart failure, such as but not limited to diuretics, ace-inhibitors, beta-blockers, angiotensin receptor blockers, isosorbide dinitrate, hydralazine, angiotensin receptor-neprilysin inhibitors, aldosterone antagonists, a PDE5 inhibitor, a statin, a neprilysin inhibitor, an aldosterone inhibitor, or an antitumor necrosis factor-alpha therapy. In one embodiment, the second agent is a statin, for example atorvastatin, fluvastatin, lovastatin, pravastatin, rosuvastatin, or simvastatin. For this purpose, the preparations administered may comprise a combination of the active ingredients in the known dosages or amounts, respectively. Likewise, the combination therapy may comprise the parallel administration of separate preparations, by the same or different routes. Optionally, the dosage of the active ingredient comprised in addition to the dose of the fumaric acid derivative administered in accordance with the present disclosure may be reduced advantageously.

In one embodiment, combination relates to (a) a compound having the formula:

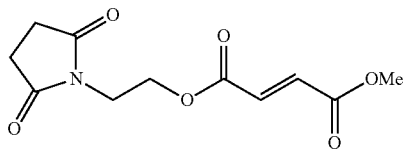 [SMILES: COC(=O)/C=C/C(=O)OCCN1C(=O)CCC1=O]

and (b) a statin for treatment of heart failure disease, including heart failure with preserved ejection fraction. In some embodiments, a pharmaceutical composition is provided comprising (a) a compound having the formula

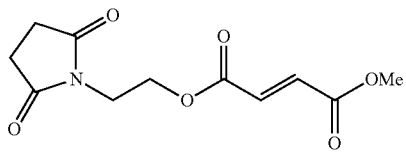 [SMILES: COC(=O)/C=C/C(=O)OCCN1C(=O)CCC1=O]

and (b) a statin. In one embodiment, a compound having the formula:

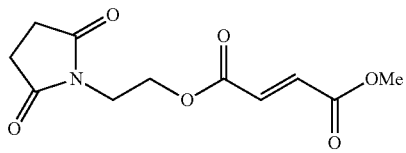 [SMILES: COC(=O)/C=C/C(=O)OCCN1C(=O)CCC1=O]

is administered at a dose range of 210 mg to 1260 mg and a statin is given at a dose range of 10 mg to 80 mg for treatment of heart failure disease, including heart failure with preserved ejection fraction. In some embodiments, the statin is selected from group consisting of atorvastatin, fluvastatin, lovastatin, pravastatin, rosuvastatin, and simvastatin.

The prodrugs of monomethyl fumarate (MMF) to be used according to the present disclosure are prepared by processes known in the art (see, for example U.S. Pat. No. 8,669,281, the disclosure of which is herein incorporated by reference in its entirety).

PROPHETIC EXAMPLE 1

The following prophetic example serves to provide approximate dosage levels of prodrugs of monomethyl fumarate to achieve the intended effect, for example treatment of heart failure with preserved ejection fraction (HF-PEF). Based on the literature, a few assumptions about the dosage can be made, as will be described in further detail below.

The full mechanism of fumaric acid esters such as dimethyl fumarate (DMF) and its primary metabolite, monomethyl fumarate (MMF), is not completely understood, but their beneficial effects appear to be mediated, at least in part, through the activation of the NRF2 antioxidant response pathway, which further increases expression of ARE, which increases expression of detoxifying enzymes and antioxidant proteins.

NRF2 deficiency, demonstrated by NRF2 knockout in marine models, results in an earlier onset of cardiac dysfunction induced by pressure and volume overload (Li et al Arterioscler Thromb Vase Biol. 2009, 29(11), 1843-50). Certain NRF2 activators such as sulforaphane, curcumin, carbobenzoxy-Leu-Leu (MG132), resveratrol, garlic organosulfur compounds, allicin, 4-hydroxynonenal (4-HNE), α-lipoic acid, hydrogen sulfate, and 17α-estradiol have been used as therapeutic targets to reduce cardiac remodeling, but prodrugs of monomethyl fumarate have not been used yet to reduce cardiac remodeling (Zhou et al; J Appl Physiol. 2015, 119(8), 944-951).

Fumarates are cardioprotective in acute situations via activation of the NRF2 pathway in acute ischemia due to myocardial infarction (Ashrafian et. al; Cell Metab. 2012, 15(3), 361-71). However, Ashrafian et. al claims that fumarates are harmful in chronic situations, including heart failure. Prodrugs of monomethyl fumarate are herein proposed to achieve the intended effect, for example, treatment of chronic heart failure with preserved ejection fraction (HF-PEF).

Dimethyl Fumarate has been tested for multiple sclerosis and psoriasis at multiple dosages in the past, including 120 mg, 240 mg, daily, BID, and TID. The side effect profile was similar regardless of which dosage was used. In order to determine dosage of a prodrug of monomethyl fumarate, a dose escalation study may be conducted to find a comparable dosage of the MMF prodrug to DMF's 240 mg dose, by comparing plasma levels of MMF. For example, one MMF prodrug known as ALKS 8700, a compound having formula:

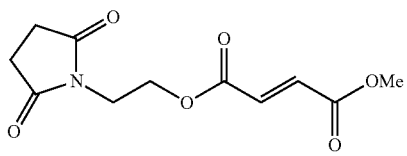 [SMILES: COC(=O)/C=C/C(=O)OCCN1C(=O)CCC1=O]

has been tested in such a way to determine that 420 mg of ALKS 8700 is a comparable dose of 240 mg DMF (Tecfidera) by comparing plasma levels of MMF. (Hunt et al. Safely, Tolerability, and Pharmacokinetics of ALKS 8700, a Novel Oral Therapy for Relapsing-Remitting Multiple Sclerosis, in Healthy Subjects). Various dosages of an MMF prodrug will be tested in HFPEF patients so that the dosage that is comparable to a DMF dosage of 120 mg, 240 mg, daily, BID, and TID may be determined. Using ALKS 8700 as one such MMF, such dosage is calculated to be 210 mg, 420 mg, daily, BID, TID in patients with HFPEF.

Furthermore, pro-inflammatory cytokines IL-6 and TNF-α are raised in HFPEF, which may lead to increase activity of VCAM, E-Selection, and NADPH oxidase, which increase ROS in coronary microvasculature endothelial cells, leading to the hallmarks of HFPEF; ventricular stiffness, impaired relaxation, and cardiac dysfunction. The prodrugs of monomethyl fumarate may reduce damage of ROS in heart failure by multiple pathways including increasing the NRF2/ARE pathway, and possibly by reducing NF-kB, which reduces IL-6 and TNF-α.

LCZ696, a combined angiotensin receptor neprilysin inhibitor (ARNI) that has recently shown to reduce mortality in HFREF but not in HFPEF patients. LCZ696 inhibits natriuretic peptide breakdown and enhances cGMP activation, and in HFPEF was associated with incremental reductions in circulating N-terminal pro-B-type natriuretic peptide (NT-proBNP) levels when compared to treatment with the ARB valsartan, alone. However, these reductions were incremental, and it is yet to be seen whether LCZ696 or other angiotensin receptor-neprilysin inhibitors will lead to any significant mortality or clinical benefit in HFPEF patients. Furthermore, the comparison with ARB valsartan alone, is flawed in that ARB valsartan is used in the treatment of HFREF but not in HFPEF.

The patients' baseline TNF-alpha, IL-6, NT-proBNP will be measured at the start of the trial and compared to levels at various intervals (weeks to months to years) to determine the ideal dosage based on reductions in TNF-alpha, IL-6, and/or NT-proBNP. Such a dosage will then be tested in a larger group of HFPEF patients to measure changes in morbidity and mortality. Thus an ideal dosage of prodrug of MMF for treating HFPEF will be comparable to a dosage of 120 mg or 240 mg, daily, BID, or TID of DMF (Tecfidera), by measuring MMF concentrations in the blood. In the case of ALKS 8700, this dosage range is 210 mg to 420 mg, daily, BID, or TID, for a range of 210 mg to 1260 mg during any given day.

PROPHETIC EXAMPLE 2

Based on the above prophetic example, an exemplary, non-limiting embodiment is described in detail below. As described herein, a user may include a male or female between the ages of 50 to 100 with ejection fraction of greater than 40%, and more likely to be a female with a documented history of high blood pressure, diabetes, and/or COPD, with at least one episode of fluid overload, or who has HFPEF or is at risk of developing (HFPEF).

The most common disease leading to HFPEF is systolic hypertension, which is present in more than 85% of patients. Patients with HFPEF have normal left ventricular (LV) end-diastolic volume and normal (or near-normal) EF and stroke volume and commonly exhibit concentric remodeling of either the LV chamber and/or cardiomyocytes.

Patients with HFPEF have a devastating 5-year mortality rate (approaching 60%), costly morbidity (6-month hospitalization rate of 50%), and debilitating symptoms (maximum myocardial oxygen consumption [$MVo_2$] averaging 14 mL/g/min).

More than half of heart failure patients have heart failure with preserved ejection fraction (HFPEF). Morbidity and mortality of HFPEF are similar to HFREF; however, medications proven effective in HFREF have not been found to be effective in HFPEF. At present there are no approved treatments to reduce mortality in HFPEF. In HFREF, medications such as beta-blockers, ace-inhibitors, angiotensin receptor blockers, isosorbide dinitrate, hydralazine, aldosterone inhibitors, and angiotensin receptor neprilysin inhibitors have been shown to provide benefit. However, these medications have not shown to be beneficial in patients with HFPEF, and are not approved therapies for HFPEF.

PROPHETIC EXAMPLE 3

The following prophetic example serves to provide a combination therapy for patients with HFPEF, which includes a prodrug of MMF with a statin. To date there has been no prospective studies of statins in patients with HFPEF. However, statins have pleotropic effects, in which they have been shown to be beneficial to non-HFPEF patients beyond what was predicted based on their ability to reduce cholesterol, likely through anti-inflammatory pathways. By combining a statin with a prodrug of MMF, a synergistic effect to reduce the ROS associated with HFPEF is expected, which in turn will reduce stiffness in HFPEF and also reduce biomarkers such as IL-6. TNF-alpha, or NT-proBNP, and ultimately improve survival in HFPEF patients. In one such example, a dose range between 210 mg to 1260 mg of MMF (ALKS 8700) is given to a patient with a statin dosage between 10 mg to 80 mg.

As used in the description and claims, the singular form "a", "an" and "the" include both singular and plural references unless the context clearly dictates otherwise. For example, the term "prodrug" may include, and is contemplated to include, a plurality of prodrugs. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or (−) 5%, 1% or 0.1%. All numerical ranges provided herein are inclusive of the stated start and end numbers. The term "substantially" indicates mostly (i.e., greater than 50%) or essentially all of a method, substance, or composition.

As used herein, the term "comprising" or "comprises" is intended to mean that the methods and compositions include the recited elements, and may additionally include any other elements. "Consisting essentially of" shall mean that the methods and compositions include the recited elements and exclude other elements of essential significance to the combination for the stated purpose. Thus, a method or composition consisting essentially of the elements as defined herein would not exclude other materials, features, or steps that do not materially affect the basic and novel characteristic(s) of the claimed disclosure. "Consisting of" shall mean that the methods and compositions include the recited elements and exclude anything more than a trivial or inconsequential element or step. Embodiments defined by each of these transitional terms are within the scope of this disclosure.

The terms "optionally" as used herein means that a subsequently described event or circumstance may but need not occur, and that the description includes instances when the event or circumstance occurs and instances in which it does not.

The examples and illustrations included herein show, by way of illustration and not of limitation, specific embodiments in which, the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of treating heart failure with preserved ejection fraction in a subject having heart failure with preserved ejection fraction, the method comprising administering to the subject a therapeutically effective amount of one or more prodrugs of monomethyl fumarate or a pharmaceutically acceptable salt, polymorph, hydrate, solvate, or co-crystal thereof.

2. The method of claim 1, wherein the heart failure with preserved ejection fraction is heart failure with ejection fraction ≥40%.

3. The method of claim 1, wherein the one or more prodrugs of monomethyl fumarate comprise a compound of Formula (I), or a pharmaceutically acceptable salt, polymorph, hydrate, solvate, or co-crystal thereof:

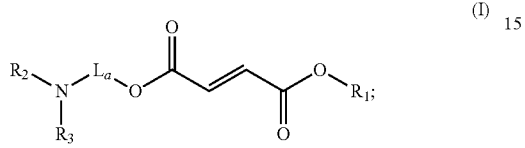
(I)

wherein:

$R_1$ is unsubstituted $C_1$-$C_6$ alkyl;

$L_a$ is substituted or unsubstituted $C_1$-$C_6$ alkyl linker, substituted or unsubstituted $C_3$-$C_{10}$ carbocycle, substituted or unsubstituted $C_6$-$C_{10}$ aryl, substituted or unsubstituted heterocycle comprising one or two 5- or 6-member rings and 1-4 heteroatoms selected from N, O, and S, or substituted or unsubstituted heteroaryl comprising one or two 5- or 6-member rings and 1-4 heteroatoms selected from N, O, and S; and $R_2$ and $R_3$ either:
(a) are each, independently, H, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_6$-$C_{10}$ aryl, substituted or unsubstituted $C_3$-$C_{10}$ carbocycle, substituted or unsubstituted heterocycle comprising one or two 5- or 6-member rings and 1-4 heteroatoms selected from N, O, and S, or substituted or unsubstituted heteroaryl comprising one or two 5- or 6-member rings and 1-4 heteroatoms selected from N, O, and S; or
(b) together with the nitrogen atom to which they are attached, form a substituted or unsubstituted heteroaryl comprising one or two 5- or 6-member rings and 1-4 heteroatoms selected from N, O, and S or a substituted or unsubstituted heterocycle comprising one or two 5- or 6-member rings and 1-4 heteroatoms selected from N, O, and S.

4. The method of claim 1, wherein the one or more prodrugs of monomethyl fumarate comprise a compound of Formula (Ia), or a pharmaceutically acceptable salt, polymorph, hydrate, solvate, or co-crystal thereof:

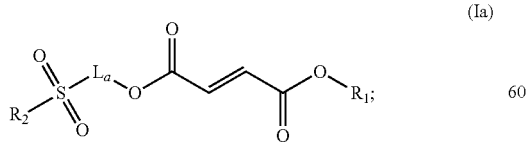
(Ia)

wherein:

$R_1$ is unsubstituted $C_1$-$C_6$ alkyl;

$L_a$ is substituted or unsubstituted $C_1$-$C_6$ alkyl linker, substituted or unsubstituted $C_3$-$C_{10}$ carbocycle, substituted or unsubstituted $C_6$-$C_{10}$ aryl, substituted or unsubstituted heterocycle comprising one or two 5- or 6-member rings and 1-4 heteroatoms selected from N, O, and S, or substituted or unsubstituted heteroaryl comprising one or two 5- or 6-member rings and 1-4 heteroatoms selected from N, O, and S; and $R_2$ is H, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_6$-$C_{10}$ aryl, substituted or unsubstituted $C_3$-$C_{10}$ carbocycle, substituted or unsubstituted heterocycle comprising one or two 5- or 6-member rings and 1-4 heteroatoms selected from N, O, and S, or substituted or unsubstituted heteroaryl comprising one or two 5- or 6-member rings and 1-4 heteroatoms selected from N, O and S.

5. The method of claim 1, wherein the one or more prodrugs of monomethyl fumarate comprise a compound of Formula (Ib), or a pharmaceutically acceptable polymorph, hydrate, solvate, or co-crystal thereof:

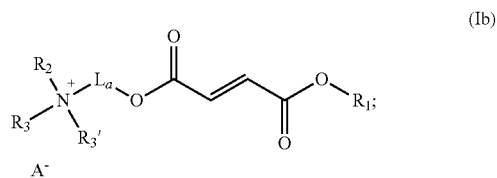
(Ib)

$A^-$ is a pharmaceutically acceptable anion;

$R_1$ is unsubstituted $C_1$-$C_6$ alkyl;

$L_a$ is substituted or unsubstituted $C_1$-$C_6$ alkyl linker, substituted or unsubstituted $C_3$-$C_{10}$ carbocycle, substituted or unsubstituted $C_6$-$C_{10}$ aryl, substituted or unsubstituted heterocycle comprising one or two 5- or 6-member rings and 1-4 heteroatoms selected from N, O, and S, or substituted or unsubstituted heteroaryl comprising one or two 5- or 6-member rings and 1-4 heteroatoms selected from N, O, and S;

$R_3'$ is substituted or unsubstituted $C_1$-$C_6$ alkyl; and either:

a. $R_2$ and $R_3$ are each, independently, H, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_6$-$C_{10}$ aryl, substituted or unsubstituted $C_3$-$C_{10}$ carbocycle, substituted or unsubstituted heterocycle comprising one or two 5- or 6-member rings and 1-4 heteroatoms selected from N, O, and S, or substituted or unsubstituted heteroaryl comprising one or two 5- or 6-member rings and 1-4 heteroatoms selected from N, O and S; or b. $R_2$ and $R_3$, together with the nitrogen atom to which they are attached, form a substituted or unsubstituted heteroaryl comprising one or two 5- or 6-member rings and 1-4 heteroatoms selected from N, O, and S, or a substituted or unsubstituted heterocycle comprising one or two 5- or 6-member rings and 1-4 heteroatoms selected from N, O and S.

6. The method of claim 1, wherein the one or more prodrugs of monomethyl fumarate comprise a compound of Formula (II), or a pharmaceutically acceptable salt, polymorph, hydrate, solvate, or co-crystal thereof:

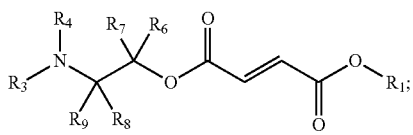

wherein:
$R_1$ is unsubstituted $C_1$-$C_6$ alkyl;
$R_4$ and $R_5$ are each, independently, H, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_6$-$C_{10}$ aryl, substituted or unsubstituted $C_3$-$C_{10}$ carbocycle, substituted or unsubstituted heterocycle comprising one or two 5- or 6-member rings and 1-4 heteroatoms selected from N, O, and S, or substituted or unsubstituted heteroaryl comprising one or two 5- or 6-member rings and 1-4 heteroatoms selected from N, O and S;
$R_6$, $R_7$, $R_8$ and $R_9$ are each, independently, H, substituted or unsubstituted $C_1$-$C_6$ alkyl, substituted or unsubstituted $C_2$-$C_6$ alkenyl, substituted or unsubstituted $C_2$-$C_6$ alkynyl or C(O)OR$_a$; and
$R_a$ is H or substituted or unsubstituted $C_1$-$C_6$ alkyl.

7. The method of claim 1, wherein the one or more prodrugs of monomethyl fumarate comprise a compound of Formula (III), or a pharmaceutically acceptable salt, polymorph, hydrate, solvate, or co-crystal thereof:

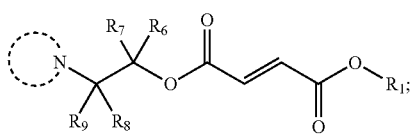

wherein:
$R_1$ is unsubstituted $C_1$-$C_6$ alkyl;

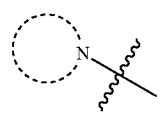

is selected from the group consisting of:

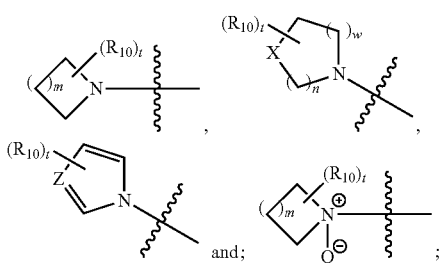

X is N, O, S, or SO$_2$;
Z is C or N;
m is 0, 1, 2, or 3;
n is 1 or 2;
w is 0, 1, 2, or 3;
t is 0, 1, 2, 3, 4, 5, 6, 7, 8, 9, or 10;

$R_6$, $R_7$, $R_8$ and $R_9$ are each, independently, H, substituted or unsubstituted $C_1$-C6 alkyl, substituted or unsubstituted $C_2$-$C_6$ alkenyl, substituted or unsubstituted $C_2$-$C_6$ alkynyl or C(O)OR$_a$; and
$R_a$ is H or substituted or unsubstituted $C_1$-$C_6$ alkyl; and
either:
a. each $R_{10}$ is, independently, H, halogen, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted $C_3$-$C_{10}$ carbocycle, substituted or unsubstituted heterocycle comprising one or two 5- or 6-member rings and 1-4 heteroatoms selected from N, O, and S, or substituted or unsubstituted heteroaryl comprising one or two 5- or 6-member rings and 1-4 heteroatoms selected from N, O, and S; or
b. two $R_{10}$ attached to the same carbon atom, together with the carbon atom to which they are attached, form a carbonyl, substituted or unsubstituted $C_3$-$C_{10}$ carbocycle, substituted or unsubstituted heterocycle comprising one or two 5- or 6-member rings and 1-4 heteroatoms selected from N, O, and S, or substituted or unsubstituted heteroaryl comprising one or two 5- or 6-member rings and 1-4 heteroatoms selected from N, O, and S; or
c. two $R_{10}$ attached to different atoms, together with the atoms to which they are attached, form a substituted or unsubstituted $C_3$-$C_{10}$ carbocycle, substituted or unsubstituted heterocycle comprising one or two 5- or 6-member rings and 1-4 heteroatoms selected from N, O, and S, or substituted or unsubstituted heteroaryl comprising one or two 5- or 6-member rings and 1-4 heteroatoms selected from N, O, and S.

8. The method of claim 1, wherein a pharmaceutical composition is administered to the subject, wherein said pharmaceutical composition comprises a therapeutically effective amount of the one or more prodrug of monomethyl fumarate that is shown to provide MMF plasma exposure comparable to dimethyl fumarate 120 mg to 720 mg per day.

9. The method of claim 1, wherein the one or more prodrugs of monomethyl fumarate comprise a compound having the formula:

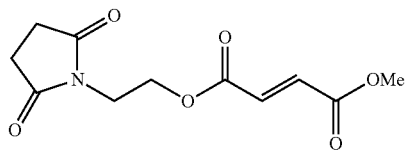 [SMILES: COC(=O)/C=C/C(=O)OCCN1C(=O)CCC1=O]

or a pharmaceutically acceptable salt thereof.

10. The method of claim 1, wherein a pharmaceutical composition is administered to the subject, wherein said pharmaceutical composition comprises 210 mg to 1260 mg of a compound having the formula:

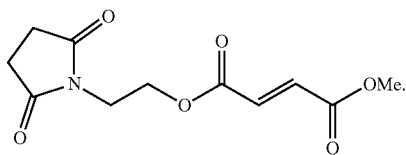 [SMILES: COC(=O)/C=C/C(=O)OCCN1C(=O)CCC1=O]

11. The method of claim 1, wherein the one or more prodrugs of monomethyl fumarate are administered in combination with one or more second agents useful for treating heart failure.

12. The method of claim 11, wherein the second agent is selected from the group consisting of: a diuretic, an ACE-inhibitor, a beta-blocker, an angiotensin receptor blocker, isosorbide dinitrate, hydralazine, an angiotensin receptor-neprilysin inhibitor, an aldosterone antagonist, a PDE5 inhibitor, a statin, a neprilysin inhibitor, an aldosterone inhibitor, and an antitumor necrosis factor-alpha therapy.

13. The method of claim 12, wherein the second agent is the statin.

14. A method of treating heart failure with preserved ejection fraction in a subject having heart failure with preserved ejection fraction, the method comprising: administering to the subject a therapeutically effective amount of (a) a compound having a formula:

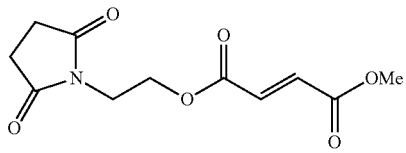 [SMILES: COC(=O)/C=C/C(=O)OCCN1C(=O)CCC1=O]

and either separately or together with (b) a statin.

15. The method of claim 14, wherein the heart failure with preserved ejection fraction is heart failure with ejection fraction greater than or equal to 40%.

16. The method of claim 1, wherein treating comprises reducing mortality or improving survival in the subject having heart failure with preserved ejection fraction.

17. The method of claim 1, wherein treating comprises increasing maximum myocardial oxygen consumption in the subject.

18. The method of claim 17, wherein the maximum myocardial oxygen consumption is increased to greater than 14 mL/g/min.

19. The method of claim 1, wherein treating comprises one or more of: reducing ventricular stiffness and improving ventricular relaxation in the subject.

* * * * *